(12) United States Patent
Biessen et al.

(10) Patent No.: US 7,273,951 B2
(45) Date of Patent: Sep. 25, 2007

(54) POLYHYDROXY PHENOLS AND THEIR USE IN BINDING P-SELECTIN

(75) Inventors: Erik Anna Leonardus Biessen, Leiden (NL); Chantal Catharina Maria Appeldoorn, Leiden (NL); Arnaud Bonnefoy, Belgium (NL); Theodorus Josephus Cornelis Van Berkel, Leiden (NL); Johan Kuiper, Leiden (NL); Marc Florimond Hoylaerts, Leuven (NL)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/558,495

(22) PCT Filed: May 7, 2004

(86) PCT No.: PCT/EP2004/004898

§ 371 (c)(1),
(2), (4) Date: Jul. 19, 2006

(87) PCT Pub. No.: WO2004/105740

PCT Pub. Date: Dec. 9, 2004

(65) Prior Publication Data

US 2006/0276545 A1  Dec. 7, 2006

(30) Foreign Application Priority Data

May 30, 2003 (EP) .................. 03012122
Feb. 3, 2004 (EP) .................. 04075320
Feb. 19, 2004 (EP) .................. 04075545
Feb. 27, 2004 (EP) .................. 04075630

(51) Int. Cl.
*C07C 229/00* (2006.01)
*C07C 69/96* (2006.01)
*A01N 37/18* (2006.01)
*A61K 38/00* (2006.01)
*A61K 51/00* (2006.01)
*A61M 36/14* (2006.01)
*C07D 209/04* (2006.01)

(52) U.S. Cl. .................. 562/450; 558/271; 514/2; 514/419; 514/469; 514/561; 424/1.21; 548/469

(58) Field of Classification Search .................. None
See application file for complete search history.

(56) References Cited

U.S. PATENT DOCUMENTS 6,410,052 B1   6/2002 Morr et al.

FOREIGN PATENT DOCUMENTS

EP  WO 03/031430 A   4/2003
GB  2 317 561 A      4/1998

OTHER PUBLICATIONS

Appeldoorn, Chantal C.M., J. Biol. Chem. (2003), 278,12,10201-10207.*
Rosenkranz, S. et al., "Inhibition of the PDGF Receptor by Red Wine Flavonoids Provides a Molecular Explanation for the "French Paradox", *The FASEB Journal*, 2002, vol. 16, pp. 1958-1976.
Yamaguchi, K. et al., "Inhibitory Effects of (-)-epigallocatechin Gallate on the Life Cycle of Human Immunodeficiency Virus Type 1 (HIV-1)", *Antiviral Research*, 2002, vol. 53, pp. 19-34.

* cited by examiner

*Primary Examiner*—Johann Richter
(74) *Attorney, Agent, or Firm*—McDonnell Boehnen Hulbert & Berghoff LLP

(57) ABSTRACT

Polyhydroxy phenols, which are non-peptidic mimetics of galloyl peptides, and a process for the preparation of gallic acid derivatives using a gallic-acid providing moiety are provided as well as polyhydroxy phenol-containing pharmaceutical and nutraceutical compositions. The use of polyhydroxy phenols as a medicament and especially for the manufacture of a medicament for the prevention, treatment or diagnosis of a disease or a condition, wherein P-selectin is involved, is provided. The same compounds can also be used as targeting tools to P-selectin expressing cells or tissues in a composition, further comprising an active compound in a vehicle.

9 Claims, 13 Drawing Sheets

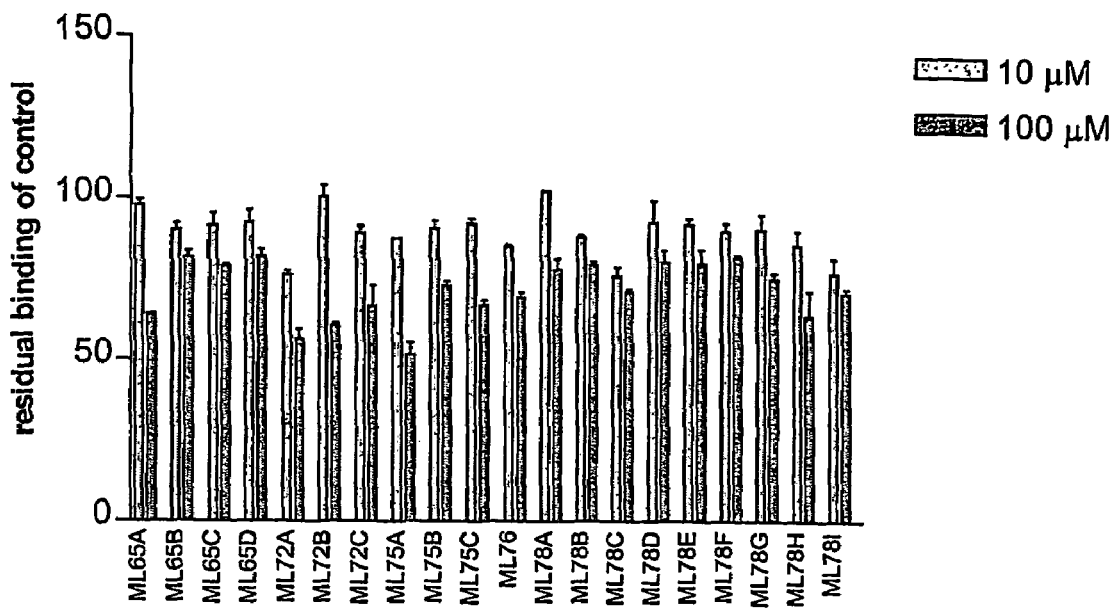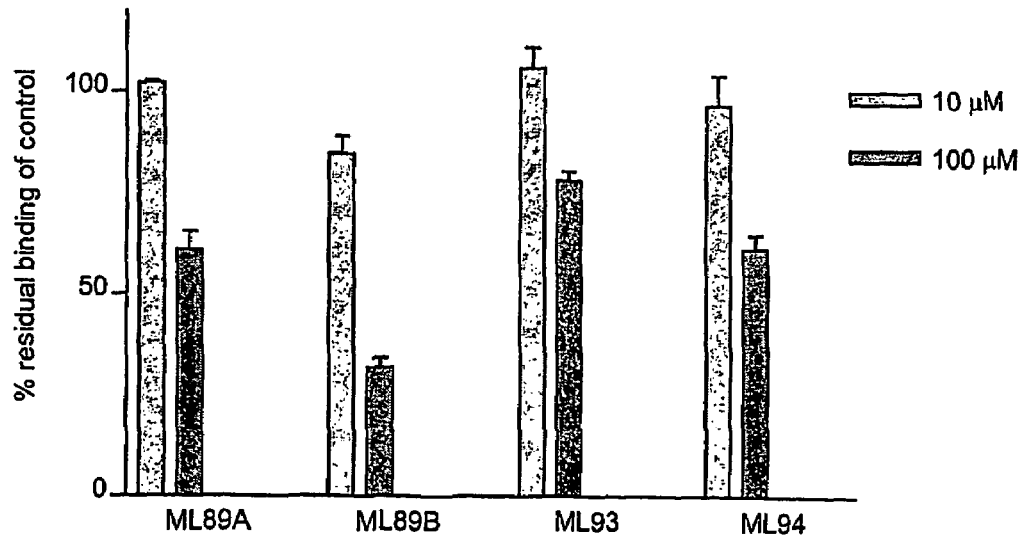
Figure 2

Figure 2
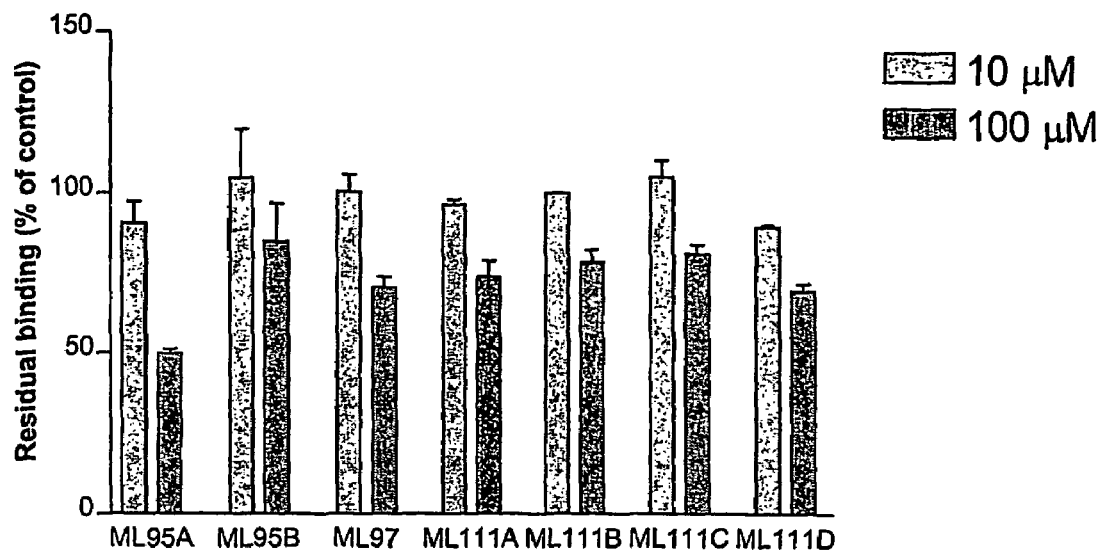
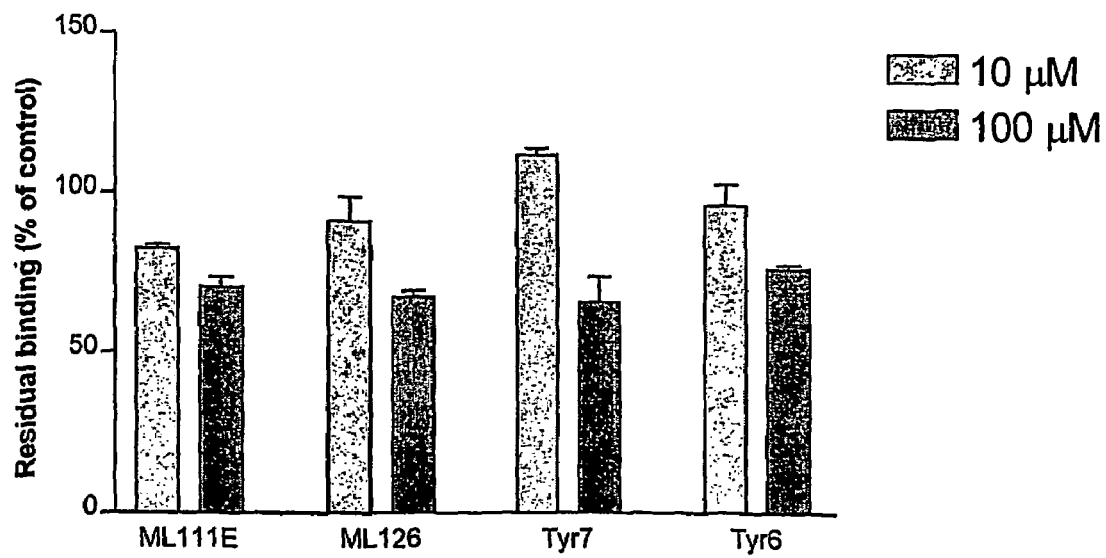

Figure 3

*In vitro* evaluation of purified Ugi products

|  | Isomer 1 | Isomer 2 |
|---|---|---|
|  | $IC_{50}$ (95% CI) | $IC_{50}$ (95% CI) |
| ML72A | 12 μM (7.4-18) | 5 μM (3.2-8.2) |
| ML75A | 18 μM (8.8-36.8) | 8 μM (2.5-23.8) |
| ML78C | 8.5 μM (3.6-20.4) | 12 μM (6.8-21.3) |
| ML78E | 25 μM (10.5-57.8) | 12 μM (2.9-48.8) |
| ML78H | 10 μM (4.5-21.2) | 3 μM (1.2-7.4) |
| ML89B | 29 μM (7.5-110.5) | *(only 1 isomer)* |
| ML95A | 23 μM (10.1-51.7) | 23 μM (11.2-47.3) |

Figure 4A and B
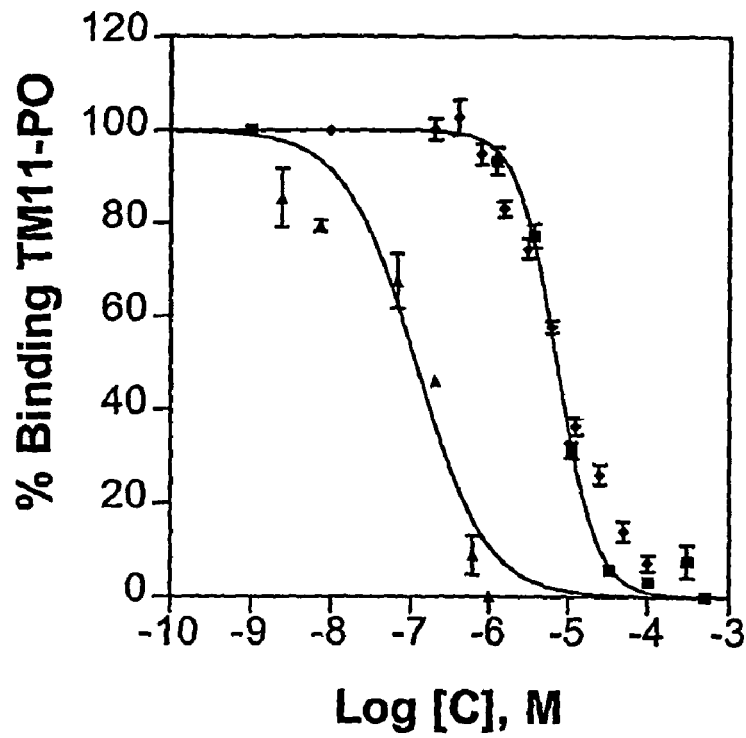
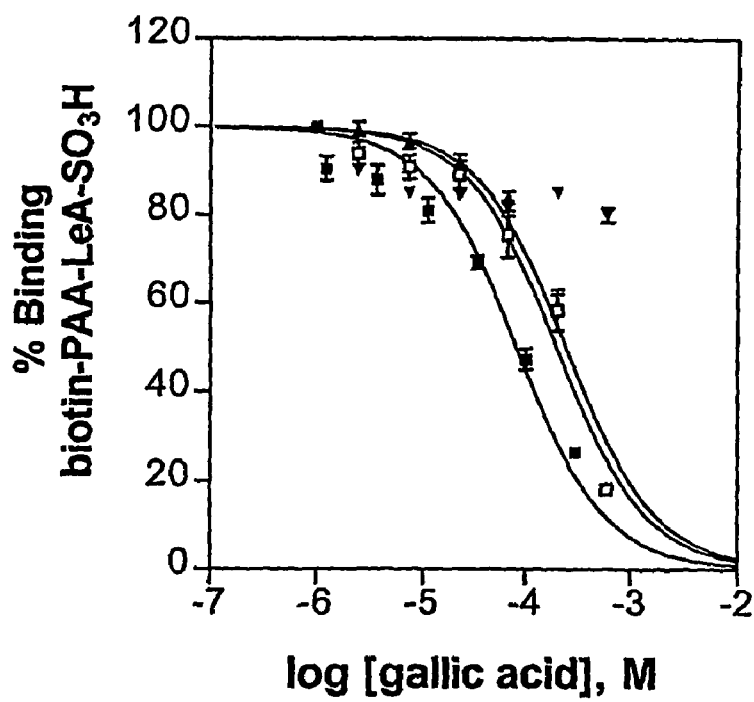

Figures 5A and B
A
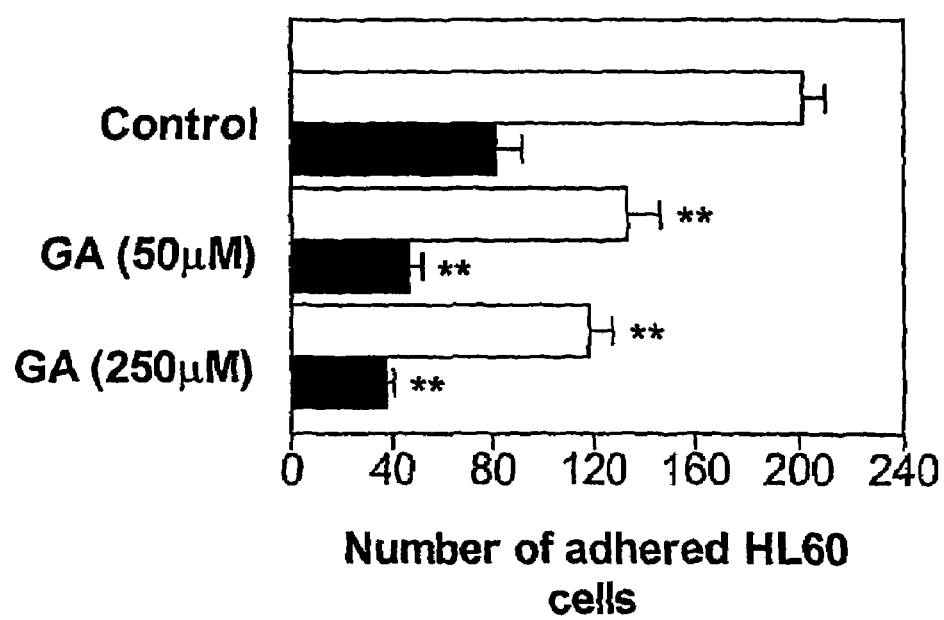
Number of adhered HL60 cells
B
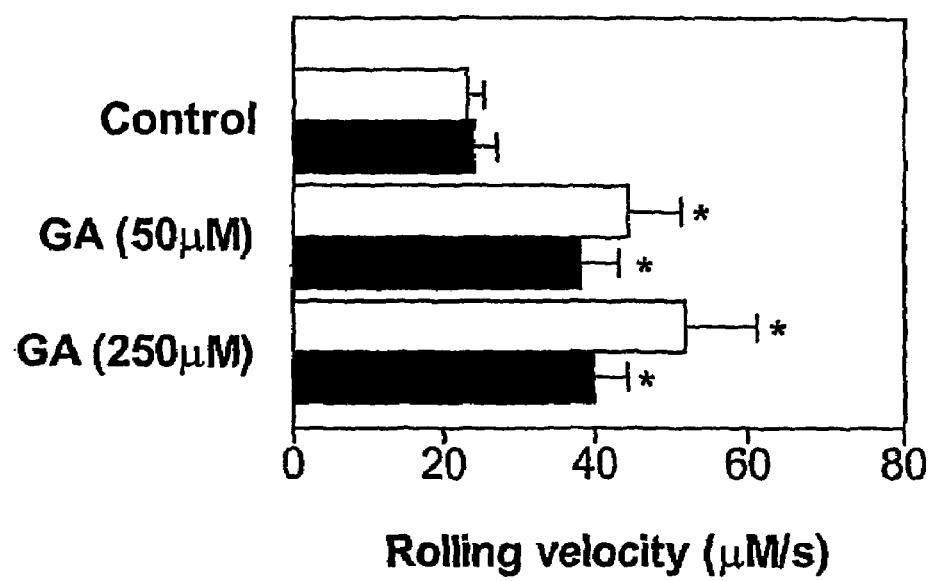
Rolling velocity (μM/s)

Conjugate rolling

Figures 8A and B
A
WT
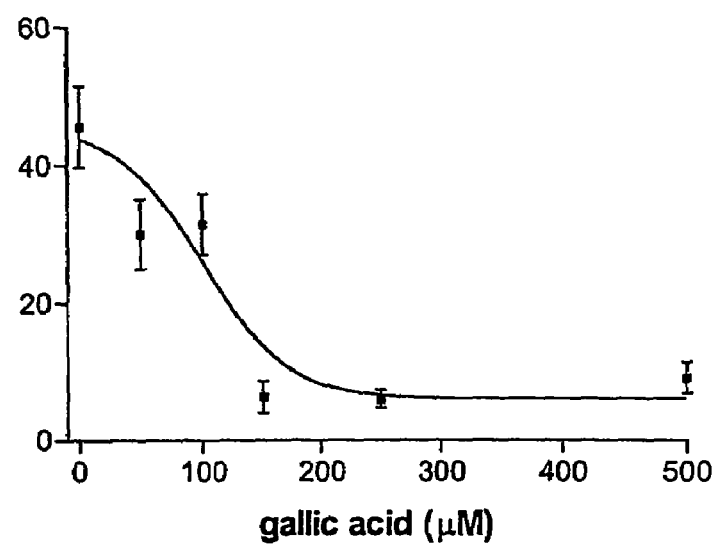
B
ApoE-/-
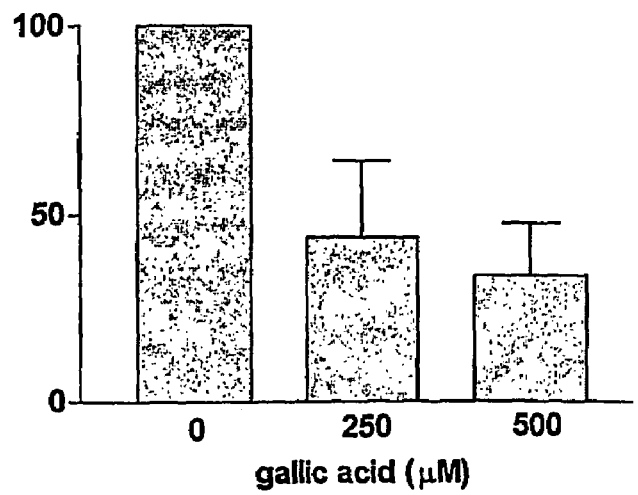

Figure 10
A
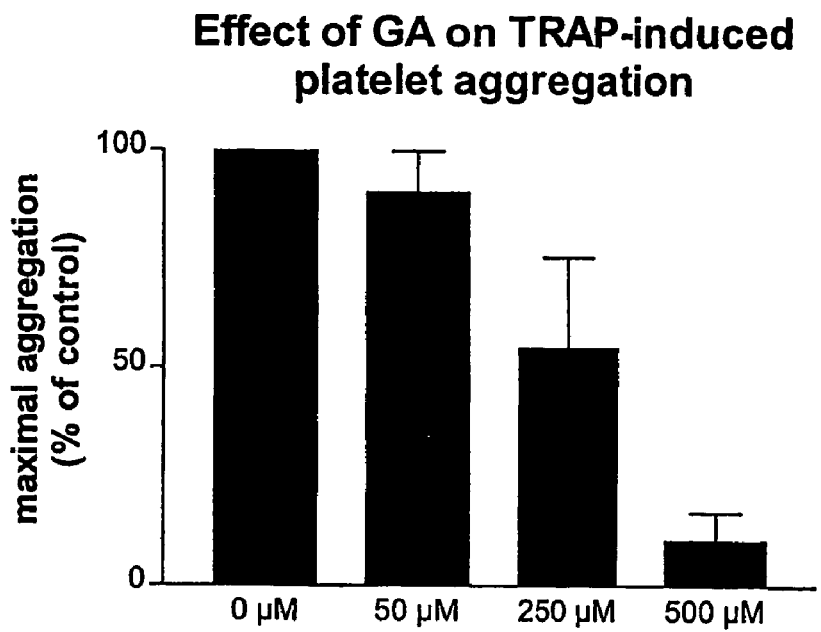
B
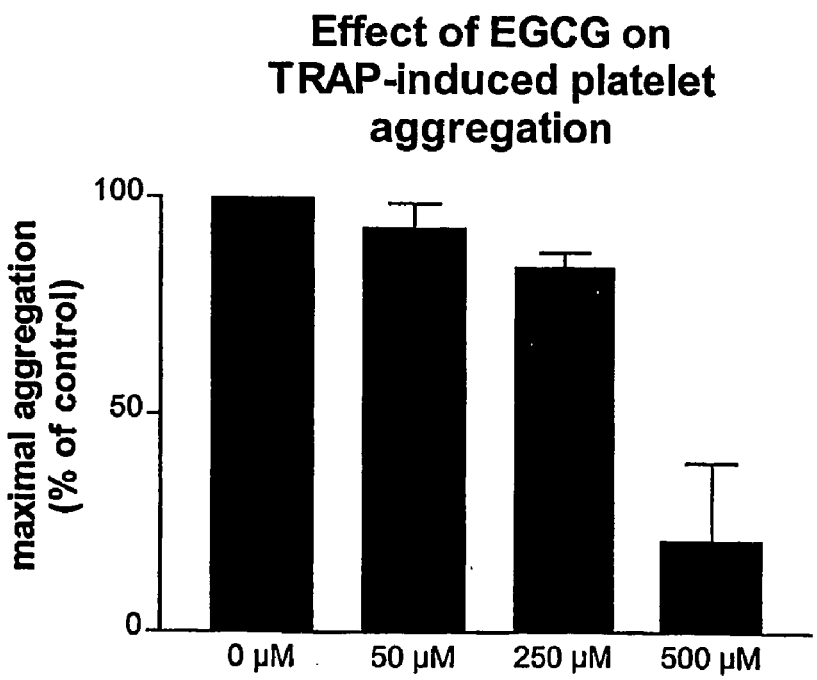

POLYHYDROXY PHENOLS AND THEIR USE IN BINDING P-SELECTIN

TECHNICAL FIELD

The present invention relates to polyhydroxy phenols, a process for the preparation of polyhydroxy phenols, compositions containing polyhydroxy phenols and the use of polyhydroxy phenols as a medicament, especially for the prevention, treatment or diagnosis of diseases or disorders wherein P-selectin is involved. In addition thereto the present invention relates to the use of polyhydroxy phenols as a targeting agent to P-selectin-expressing cells.

BACKGROUND OF THE INVENTION

In recent years, coronary artery disease (CAD) has become a major cause of death in western societies. Hyperlipidemia and atherosclerosis are regarded as major risk mechanisms for coronary diseases, whereas there is some evidence that hypertension, diabetes and excess body weight may have less negative impact on coronary disorders than previously assumed.

Atherosclerosis is thought to be initiated at critical sites of the arterial vasculature by a process of monocyte adhesion to the vessel wall, sustained by the occurrence of active functional changes on the endothelial surface (M. A. Gimbrone et al., Thromb. Haemost. 82(2) 722-6 (1999)).

Blood platelets play a major role in coronary artery disease (B. A. Osterud, Thromb. Res. 85: 1-22 (1997)). Platelets are found at the sites of early atherosclerotic lesions. When activated, platelets secrete potent mitogenic factors such as platelet-derived growth factor, transforming growth factor β, and epidermal growth factor, which lead to smooth muscle proliferation and progression of atherosclerotic lesions. Enhanced platelet reactivity and spontaneous platelet aggregation were associated with a higher risk of recurrent coronary artery disease. Physiologic anti-platelet metabolites, such as nitric oxide, activate platelet guanylate cyclase and elevate cyclic guanosine-3',5'-monophosphate, thereby reducing fibrinogen binding to the glycoprotein IIb-IIIa (GPIIb-IIIa) receptor through inhibition of agonist-mediated calcium flux.

Several interventions demonstrated a decreased risk of cardiovascular disease, such as with therapeutic doses of aspirin (R. Collins et al., N. Eng. J. Med. 336: 847-60 (1997)) and antioxidant supplements (C. H. Hennekens, Am. Heart J. 128: 1333-6 (1994)). Therapy with anti-platelet agents such as aspirin and clopidogrel significantly decreases the incidence of primary and secondary coronary events (C. H. Hennekens, Annu. Rev. Public Health 18: 37-49 (1997)). Antibodies and peptides that block the fibrinogen binding to activated platelet glycoprotein IIb-IIIa have improved the results of coronary revascularisation procedures. Activation-dependent platelet antigens also indicate changes in platelet function after physical exercise, physiologic challenges (D. Rajasekhar, Thromb. Haemost. 77: 1002-7 (1997)), and dietary intervention (M. A. Allman-Farinelli et al., Thromb. Res. 90: 163-9 (1998)).

In recent years, certain dietary components, notably unsaturated fatty acids and polyphenols, have been identified as key mediators in numerous cellular processes. As observed by De Caterina et al. (Atheriosler. Thromb. 14: 1829-36 (1994); Prostaglandins Leukot. Essent. Fatty Acids 52: 191-5 (1995)), ω-3 fatty acids, which have effects on total and LDL cholesterol and yet also appear to be linked to protection from atherosclerosis, may act by inhibiting early atherogenic events related to monocyte adhesion to endothelial cells. This process occurs through inhibition of endothelial activation, i.e. the concerted expression of cytokine-inducible endothelial leukocyte adhesion molecules and leukocyte chemo-attractants affecting monocyte adhesion. Inhibition of a common signal-transduction pathway involving the transcription factor nuclear factor-κB (NF-κB) was therefore suggested.

The involvement of nuclear factor-κB has been established by M. A. Carluccio et al. (Atherioscler. Thromb. Vasc. Biol. 23(4): 622-629 (2003)). They demonstrated that oleuropein and hydroxytyrosol (major components of olive leaf extract) inhibit at nutritionally relevant concentrations transcriptional endothelial adhesion molecule expression, thus possessing atheroprotective features.

Several epidemiological and laboratory studies indicate that moderate alcohol consumption can lower the risk of atherosclerosis and hyperlipidemia and thus the chance of coronary artery disease (E. B. Rimm et al., BMJ 312: 731-36 (1996); D. M. Goldberg et al., Clin. Chim. Acta 237: 155-187 (1995)). In France, where the red wine consumption is relatively high as compared to Northern European Countries and the USA, but the pattern of saturated fat intake similar, the mortality rate of CAD is approximately 50% lower. This so called "Trench Paradox" (S. Renaud et al., Lancet 339: 1523-1526 (1992)) has been attributed to the major constitute of "wine tannins" the polyphenolic alcohols, such as gallic acid and flavonoids of the catechin family including (+)-catechin, (−)-epicatechin, and procyanidin B2, which are abundantly present in red wine (S. Rosenkranz et al., Faseb J. 16: 1958-1976 (2002); P. M. Kris-Etherton et al., Am. J. Med. 113, Suppl. 9B: 71-88 (2002)).

Phenolic substances contained in red wine have been found to inhibit oxidation of human LDL and thus postulated to possess atheroprotective properties. However, it is difficult to attribute a reduction of atherosclerotic processes and consequently protection from coronary artery disease only to the inhibition of LDL oxidation because many vascular effects of antioxidants are not related to the resistance of LDL to oxidation (M. N. Diaz et al., N. Eng. J. Med. 337: 408-416 (1997)).

Several studies carried out in humans and animals have shown that wine phenolic compounds could exert their effects by reducing prostanoid synthesis from arachidonate. In addition, it has been suggested that wine phenolic fractions could reduce platelet activity mediated by nitric oxide. Moreover, wine phenolic components increase vitamin E levels, while decreasing the oxidation of platelets submitted to oxidative stress.

M. E. Ferrero et al. (Am. J. Clin Nutr. 68: 1208-14 (1998)) showed the role of resveratrol (a polyphenol present in red wine) in the regulation of the endothelial cell adhesion molecule-1 expression, and thus demonstrated that its anti-atherogenic activity is not in the front rank related to the protection of LDL from oxidation as postulated by M. N. Diaz et al. (ibid).

S. Rotondo et al. (Br. J. Pharmacol. 123(8): 1691-99 (1998)) investigated the effect of trans-resveratrol on functional and biochemical responses of polymorphonuclear leukocytes (PMN), which are suggested to be involved in the pathogenesis of acute coronary heart diseases. The results of their studies indicate that trans-resveratrol interferes with the release of inflammatory mediators by activated PMN and down-regulates adhesion-dependent thrombogenic PMN functions.

M. A. Carluccio et al. (Atheriscler. Thromb. Vasc. Biol. 23(4): 622-29 (2003)) confirmed recently the conclusions by Ferrero et al. and S. Rotondo et al. establishing the involvement of nuclear factor-κB as key transcription factor for the endothelial cell adhesion molecule-1 expression.

D. Rein et al. (Am. J. Clin. Nutrition 72(1): 30-35 (2000); J. of Nutrition 130 (8S): 2120S-2126S (2000)) executed a series of in vitro and in vivo studies on the effects of cocoa procyanidins (trimers and pentamers), epicatechin and de-alcoholised wine (DRW) on platelet activation. Fluorescent-labeled monoclonal antibodies recognizing the fibrinogen binding conformation of GPIIb-IIIa (PAC-1 binding) and the activation-dependent platelet epitope CD62P (P-selectin) were selected as markers for the platelet activation. Both tested components added to whole blood in vitro increased PAC-1 binding and P-selectin expression on unstimulated platelets, but suppressed the platelet activation in response to epinephrine. In contrast, cocoa procyanidins inhibited stimulated platelet activation in whole blood, whereas the effect of de-alcoholised wine was not that much pronounced. Generally, this suppressive effect observed on platelet reactivity may explain the cardioprotective effects of polyphenols present in wine or other nutritional preparations (e.g. cocoa beverages and chocolate).

Red wine polyphenols and their impact on platelet aggregation have been moreover studied by P. Russo et al. (Nutr. Metab. Cardiovasc. Dis. 11(1): 25-9 (2001)). They have isolated four classes of wine phenolic compounds: phenolic acids (fraction 1), procyanidins, catechins and monomeric anthocyanidins (fraction 2), flavonols and resveratrol (fraction 3) and polymeric anthocyanidins (fraction 4). The effect of each fraction on ADP-induced platelet aggregation in rats and c-AMP content was compared with that of de-alcoholised red wine (DRW) and the pure phenolic compounds alone (quercetin, catechin, resveratrol, caffeic acid). Both DRW and the phenolic fraction 2 inhibited significantly ADP-induced platelet aggregation, whereas the effects of fractions 3 and 4 and the pure phenolic compounds were not significant. A significant increase in platelet c-AMP content was observed first after the addition of DRW and fraction 2.

As another approach to exhibit the impact of polyphenols in red wine on the platelet activation and consequently their atheroprotective properties, A. D. Blann et al. (Blood Coagul. Fibrinolysis 13(7): 647-651 (2002)) explored markers of platelet activity (beta-thromboglobulin and soluble P-selectin) and endothelial cell function (von-Willebrand-factor and soluble thrombomodulin) before and upon ingestion of red wine in vivo. The only significant increase was noticed for beta-thromboglobulin. The study results led to the conclusion that red wine activates the platelets without having any substantial effect on the endothelium.

Rosenkranz et al. (Faseb J. 16: 1958-1976 (2002)) observed that non-alcoholic constituents of red wine that accumulate during mash fermentation act as potent inhibitors of platelet-derived growth factor β (βPDGFR) signalling and PDGF-dependent cellular responses in vascular smooth muscle cells (VSMC). Signals initiated by the βPDGFR play an important role in vascular development and the pathogenesis of atherosclerosis. PDGF-dependent migration and proliferation of VSMC are critical steps during atherogenesis. In the same work they demonstrated that mainly the flavonoids of the catechin family inhibit the PDGF-dependent tyrosine phosphorylation of the βPDGFR, whereas gallic acid only does not mediate a significant effect.

Furthermore, it is known from U.S. Pat. No. 6,133,311 that gallic acid inhibits the activities of 3-hydroxy-3-methyl-glutaryl-Coenzyme A (HMG-CoA reductase), which mediates the synthesis of mevalonic acid, an intermediate in the biosynthesis of sterols, e.g. cholesterol, or isoprenoids (William W. Parmley and Kanu Chatterjee (Eds.), Cardiovascular Pharmacology, Wolfe Publishing, 1994). Thus, it reduces the rate of cholesterol biosynthesis and prevents therefore arteriosclerosis and hypercholesterolemia which are known to be strongly related to CAD.

In U.S. Pat. No. 6,133,311, an additional mechanism of action is proposed for gallic acid when used to control increased plasma cholesterol level. They are referring to an interaction of gallic acid with the acyl CoA-cholesterol-o-acyltransferase (ACAT). ACAT promotes the esterification of cholesterol in blood. Foam cells are formed by the action of ACAT and contain a large amount of cholesterol ester carried by low density lipoprotein (LDL) in the blood (D. T. Witiak and D. R Feller (Eds.), Anti-Lipidemic Drugs: Medicinal, Chemical and Biochemical Aspects, Elsevier, pp 159-195 (1991)). The formation of foam cells in the arterial wall increases with the ACAT activity. Accordingly, as gallic acid inhibits the action of ACAT, it may also lead to prevention of atherosclerosis and hyperlipidemia.

P-selectin is a key mediator in a variety of inflammatory processes and is implicated in, for instance, atherosclerosis and thrombosis. Therefore, the blocking of P-selectin is an attractive strategy for the treatment of these important diseases. Previously, a number of oligopeptides (with a consensus sequence Trp-Val-Asp-Val) was identified as selective P-selectin antagonists, displaying low micromolar affinity (WO 03/020753). Moreover, nanomolar range inhibitors could be obtained by functionalising the N-terminus of this and similar sequences with a galloyl (3,4,5-trihydroxybenzoyl) group (non pre-published international patent application PCT/EP03/07260).

Notwithstanding the increased understanding of some of the major diseases including coronary artery disease and atherosclerosis, and the availability of new compounds and methods to control the above-mentioned diseases and conditions to some degree, there still is a need for further improvements, both with respect to potent compounds and to methods to control or antagonise the effects of P-selectin activation in humans and to methods which reduce the risk of developing diseases associated with P-selectin activity which are cost-effective, acceptable to large fractions of the population, safe and tolerable. Finally there is a need for improved methods which can be used for early diagnosis of conditions leading to P-selectin associated diseases.

SUMMARY OF THE INVENTION

The object of the invention is to provide polyhydroxy phenols, which are non-peptidic mimetics of galloyl peptides, and a process for the preparation of the polyhydroxy phenols using a gallic-acid providing moiety.

A further object of the invention is to provide polyhydroxy phenol-containing pharmaceutical and nutraceutical compositions.

Further, the use of polyhydroxy phenols as a medicament and especially for the manufacture of a medicament for the prevention, treatment or diagnosis of a disease or a condition, wherein P-selectin is involved, is provided.

Finally the use of polyhydroxy phenols as a targeting tool to P-selectin expressing cells or tissues in a composition, further comprising an active compound in a vehicle, is provided.

DETAILED DESCRIPTION

The present inventors have found polyhydroxy phenols of structural formula:

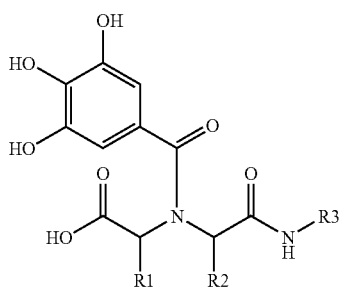

wherein:
- $R^1$=a hydrogen; a straight or branched ($C_1$-$C_4$)aliphatic alkyl group or an aromatic group, optionally respectively substituted by a hydroxyl group, a carboxylic acid group, an amino group or a straight or branched ($C_1$-$C_4$)aliphatic alkyl group. Preferably $R^1$=ethyl, phenylmethyl, indolylmethyl or 4-hydroxyphenylmethyl.
- $R^2$=an optional group, being a straight or branched ($C_1$-$C_4$)aliphatic alkyl group. Preferably $R^2$=a straight ($C_1$-$C_4$)aliphatic alkyl group and more preferably $R^2$=hydrogen, ethyl, propyl or isopropyl.
- $R^3$=a straight or branched ($C_1$-$C_4$)aliphatic alkyl group, optionally substituted by one or more carboxylic acid group, or a straight or branched ($C_1$-$C_4$)aliphatic alkyl amide group; or a ($C_3$-$C_8$) cycloalkyl group, optionally substituted by a straight or branched ($C_1$-$C_4$) aliphatic alkyl group or one or more carboxylic acid group. Preferably $R^3$=a straight ($C_1$-$C_4$)aliphatic alkyl group, substituted by one or two carboxylic acid group, optionally substituted by a straight or branched ($C_1$-$C_4$)aliphatic alkyl group and more preferably $R^3$=ethylcarboxylic acid or propyldicarboxylic acid.

In addition to the above-provided explanation in the present invention a straight or branched ($C_1$-$C_4$)aliphatic alkyl group exemplifies methyl, ethyl, propyl, isopropyl, butyl, isobutyl and the like. An aromatic group is one having 6 to 14 carbon atoms and comprises a carbocyclic aryl and a heterocyclic aryl group. The carbocyclic aryl group is monocyclic to tricyclic and preferably is phenyl, naphthyl, anthryl, or phenantryl and the like.

The heterocyclic aryl group is a monocyclic to tricyclic group having from 1 to 4 heteroatoms, selected from the group consisting of nitrogen atom, oxygen atom, or sulfur atom. The heterocyclic group is pyrrolyl, pyrazolyl, imidazolyl, thiazolyl, oxazolyl, isothiazolyl, isooxazoryl, 1,3,5-triazolyl, 1,2,4triazolyl, 1,3,5-thiadiazolyl, 1,3,5-oxadiazolyl, pyrizyl, pyridazinyl, pyrimidyl, pyrazyl, benzofuranyl, isobenzofuranyl, benzothienyl, indolyl, chromenyl, quinolyl, isoquinolyl, phthalazinyl or quionoxalinyl and the like.

The ($C_3$-$C_8$) cycloalkyl group represents cyclopropyl, cyclobutyl, cyclopentyl, cyclohexyl, cycloheptyl or cyclooctyl. Moreover, the ($C_3$-$C_8$) cycloalkyl group is optionally substituted by a straight or branched ($C_1$-$C_4$)aliphatic alkyl group, or one or more carboxylic acid groups.

The polyhydroxy phenols according to the present invention can be prepared in a variety of ways. A preferred manufacturing method will be selected, dependent of the substituents in the polyhydroxy phenol, the availability of starting materials, efficiency and costs.

For the construction of a biased library of compounds, in accordance with the present invention, it has appeared to be very convenient to use the solid phase Ugi four component reaction (Ugi-4CR), as has been described in detail in the examples. Solid-phase Ugi reactions are already known in the art. For further information the reader is referred to e.g. S. W. Kim, S. M. Bauer and R. W. Armstrong (1998) Tetrahedron Lett., 39: 6993-6996; S. W. Kim, Y. S. Shin and S. Ro (1998) Bioorg. Med. Chem. Lett., 8: 1665-1668; P. A. Tempest, S. D. Brown and R. W. Armstrong (1996) Angew. Chem. Int. Ed. Engl., 35: 640-643.

In the first instance, the reaction components were chosen in a biased fashion, based upon the functionalities present in one of the most potent antagonists found to date, galloyl-Trp-Val-Asp-Val-OH. The components were chosen from amino acids (bound to a solid support), aliphatic aldehydes and carboxyl-containing nitriles.

Gallic acid did not show to be in the most appropriate form for carrying out the Ugi four components and obtaining products in a high yield. In order to improve the yield of the process a new gallic acid providing entity was developed, viz. the highly conveniently protected gallic acid building block, 3,4,5-tri-O-(tert-butoxycarbonyl)-gallic acid.

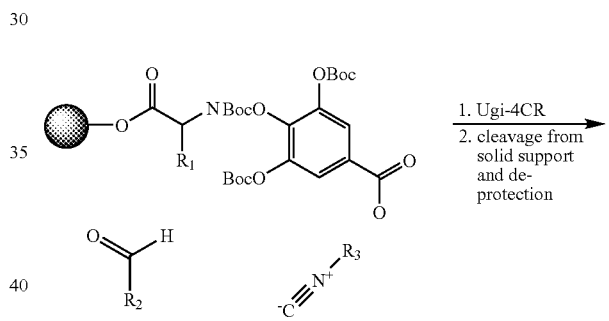

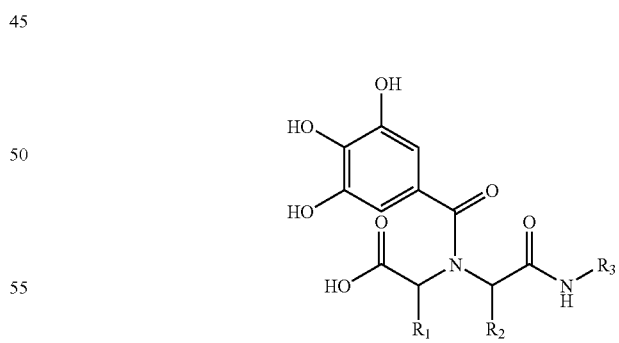

Using the Ugi four component reaction, a series of gallic acid containing peptide-like structures was synthesized and their P-selectin blocking potency was evaluated. Inspired by the high potency of the GaWVDV antagonist (see the figure below for the structural formula), it was decided to choose the reaction components in such a way that the Ugi products reflect the functionalities present in that antagonist (see below).

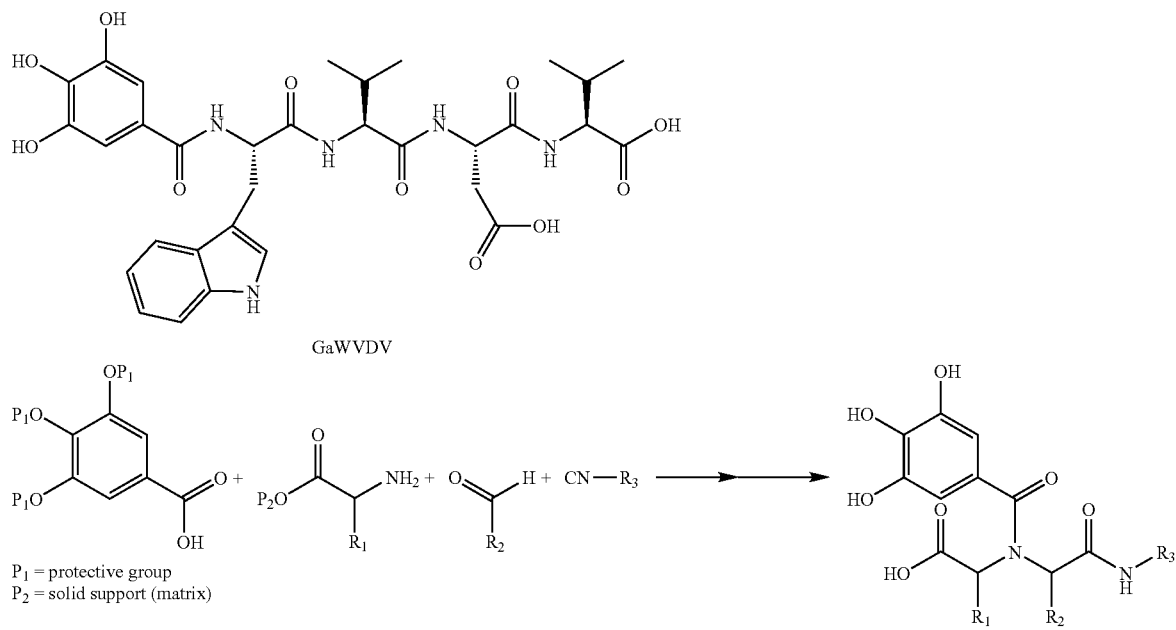

The gallic acid-providing moiety 3,4,5-tri-O-(tert-butoxy-carbonyl)-gallic acid has shown to be a highly convenient building block for the preparation of polyhydroxy phenols, more in particular galloyl peptides or a functional equivalent thereof or non-peptidic mimetics of galloyl peptides, such as the polyhydroxy phenols in accordance with the present invention, having the structure as shown above.

During the above-described Ugi four component reaction an amino acid, an aliphatic aldehyde, a nitrile and a gallic acid-providing moiety are combined. In this process any amino acid may be used. The term amino acid should be understood as to comprise both naturally occurring amino acids and synthetically prepared compounds, which are represented by the general formula HOOC—C—($NH_2$)—$R^1$, wherein $R^1$ has the meaning as described above. As the aliphatic aldehyde a straight or branched ($C_1$-$C_4$)aliphatic aldehyde is used, such as propionaldehyde, butyraldehyde or isobutyraldehyde. However, since not all of the starting compounds for this reaction were commercially available or available in the most appropriate form, the nitrles in accordance with the process of the present invention had to be prepared by the inventors. The method of preparation is described in the examples.

Thus, amino acids (as provider for $R^1$), aliphatic aldehydes (as provider for $R^2$) and nitriles (as provider for $R^3$) were chosen as well as cyclohexyl nitrile as a control nitrile. A library of compounds was constructed (for a phenylalanine (Phe) series, for a tryptophan (Trp) series, for a tyrosine (Tyr) series and for other amino acids, see below) on a solid support. All products (diastereoisomeric mixtures) were obtained in purities ranging from 35% to 75%.

The crude mixtures were evaluated at 10 and 100 μM in competition ELISAs using strep-AP. Preliminary screening revealed a number of trends: 1) the Phe-series and Tyr-series appears to be somewhat more active than the Trp-series and compounds constructed with other amino acids, 2) the products containing branched alkyl chains are consistently less active than the ones with linear chains and 3) a C-1 tethered carboxylic acid as $R_3$ substituent is disfavoured compared to a C-2 tether.

Next, the most promising compounds were purified and the isomers were separated in order to establish $IC_{50}$-values. Initial tests showed that ML72A was the most active of this selection with $IC_{50}$-values of 12 and 5 μM for the different isomers. ML75A was slightly less active (18 and 8 μM). Although the compounds from the Trp-series are obviously active, they consistently exhibited irregular inhibition curves, making it rather difficult to establish reliable $IC_{50}$-values. The assay is currently being optimised for the Trp-compounds. Finally, several further compounds were prepared, based on the most promising structures to establish the influence of the various substituents, and tested.

In view of the promising effects shown in various tests, the present invention further provides the polyhydroxy phenols having the structural formula as described above as a medicament.

In another embodiment, the polyhydroxy phenols having affinity to human P-selectin are not primarily used as P-selectin antagonists, but as a targeting agent or a homing device, either in combination with a drug delivery system or conjugated to a drug or active compound optionally through a linker. More in particular, preferable embodiments of a drug delivery system are a drug carrier, a targeting composition and a binding inhibitor. These embodiments mean the concrete exemplifications described below. A drug carrier for a disease or condition, wherein P-selectin is involved, comprises a polyhydroxy phenol. A targeting composition for delivery of a drug to the lesion, wherein P-selectin is involved, so to P-selectin expressing cells, comprises a drug, a polyhydroxy phenol according to the structural formula as described above and a pharmaceutically acceptable excipient.

In another embodiment is a method for delivering a drug to the lesion, wherein P-selectin is involved, characterised in that a composition comprising a drug and the polyhydroxy phenol and/or a polyphenol as a targeting agent is administered orally or parenterally. Another embodiment of the conjugate is a construct, consisting of an active compound, which is coupled via an esterase-labile linker to a residue of a polyhydroxy phenol according to the invention.

It is also possible to use the above-mentioned systems as an imaging tool, whereby the active compound is substituted by a contrast agent or a radionuclide.

The polyhydroxy phenols can also be directly coupled to the active compounds that are to be delivered to such targets. Alternatively, they can be incorporated into or anchored onto the surface of larger vehicles or entities, which are liposomes or other lipid vesicles, emulsion droplets, polymers, nano- or microparticles (including nanospheres, nanocapsules, microspheres, microcapsules etc.), hydrogels, complexes or virosomes and the like to obtain targeted vehicles for drugs or genetic material which is delivered to P-selectin expressing cells or tissues. Also multimeric presentation of the polyhydroxy phenols is to be accompanied by a higher affinity for P-selectin.

Further polyhydroxy phenols useful as a targeting agent to P-selectin-expressing cells or for preparing a medicament for the prevention, treatment or diagnosis of a P-selectin-associated disease or condition include gallic acid, gallic acid derivatives and compounds that are chemically related to gallic acid or including one or more gallic acid moieties. Also included are (precursor) compounds which, after administration, undergo chemical or enzymatic degradation to produce in situ gallic acid, the gallic acid derivative or the compound that is chemically related to gallic acid includes one or more gallic acid containing moieties. Gallic acid derivatives according to the invention include chemical structures derived from gallic acid, such as conjugates, dimers, multimers, salts, esters, ethers, amides etc. Furthermore, the derivatives include those compounds which differ from gallic acid chemically to some degree, such as by the number and/or position of phenolic hydroxyl groups or by the presence of one or more additional substituents, but which have affinity to P-selectin Gallic acid, or 3,4,5-trihydroxybenzoic acid, is a natural polyhydroxy phenol found in fruits, vegetables and herbs, such as in gall nuts, walnuts, mango seeds, red grapes, green tea and olive oil. In many plant products gallic acid is contained in the form of precursors such as tannic acid, also named tannin or gallotannin, which describes a class of compounds with a complex and non-uniform chemical structure. Tannins may be divided into 2 groups: (a) derivatives of flavanols, so-called condensed tannins and (b) hydrolysable tannins (the more important group) which are esters of a sugar, usually glucose, with one or more trihydroxybenzenecarboxylic acids. Gallic acid is a major hydrolysis product of tannin.

Gallic acid possesses very low toxicity, which is a significant advantage of the use of the invention compared to other uses applying novel inhibitors of P-selectin which tend to be toxic in low doses, or whose physiological tolerability has yet to be established.

Examples of other polyhydroxy phenols are: n-dodecyl gallate, caffeic acid and 3,4,5-trihydroxy cinnamic acid.

Likewise, polyphenols have shown to be useful to more or less the same extent as the polyhydroxy phenols, which are gallic acid and derivatives thereof Polyphenols are defined as compounds, that include more than one 6 carbon atoms-bearing aromatic ring, having one or more hydroxyl groups attached thereto. Examples of such polyphenols are (−)-epigallocatechin gallate, (epi)catechin, m-galloyl gallic acid and ellagic acid.

These polyhydroxy phenols and polyphenols however have an affinity in the micromolar range, such as expressed by an $IC_{50}$ value of less than 1000 µM, preferably less than 300 µM. More preferred are derivatives with an affinity in the middle or low micromolar range, such as an $IC_{50}$ of less than 200 to 100 µM. Another preferred range of affinity is that in the lower micromolar or even submicromolar region, such as expressed by an $IC_{50}$ of less than 100 to 50 µM, or of less than 10 or even 1 µM. They can be used either alone or in combination with the polyhydroxy phenols, as described above, in targeting compositions or in pharmaceutical compositions for the prevention, treatment or diagnosis of a disease or condition, in which P-selectin is involved, as further described in the present application.

The invention also relates to pharmaceutical or nutraceutical compositions comprising a polyhydroxy phenol having affinity to P-selectin.

As used herein, the term pharmaceutical composition refers to therapeutic and diagnostic compositions, as well as to medicaments and diagnostics containing such compositions. Therapeutic compositions and medicaments are used for the prevention or treatment of diseases and other conditions of individuals of which conditions improvement is desirable. Diagnostics and diagnostic compositions are used for the diagnosis of such diseases in vivo and in vitro. Preferred are therapeutic compositions or medicaments to prevent or improve diseases and conditions involving P-selectin. The compositions can also be used for treating diseases in which the inhibition of P-selectin-mediated intracellular signalling is desirable.

Nutraceutical compositions include all compositions typically understood as functional foods or food additives. Nutraceuticals also comprise products isolated or purified from foods and generally formulated in a fashion similar to pharmaceutical dosage forms not usually associated with food and which have demonstrated to have a physiological benefit, or provide protection against chronic disease.

Nutraceutical compositions are typically formulated and processed for oral use, while the pharmaceutical compositions containing gallic acid or a gallic acid derivative having affinity to P-selectin may be adapted for various routes of administration, such as oral, parenteral, transmucosal, nasal or pulmonary. Preferred are compositions for parenteral and oral use, and especially preferred are formulations adapted for oral administration. In this document the term formulations is used for such nutraceutical and pharmaceutical compositions and the terms per oral and oral are used interchangeably.

The pharmaceutical compositions preferably contain one or more active compounds as defined above and at least one pharmaceutical excipient. As used herein a pharmaceutical excipient is any pharmaceutically acceptable substance or mixture of substances having no substantial pharmacological activity, which can be used as a vehicle or as an auxiliary substance to formulate a compound into dosage form which is stable and easy to administer. Examples of pharmaceutically acceptable excipients are found in the monographs of all major pharmacopoeias.

Appropriate dosage forms for per oral administration include solid dosage forms such as tablets, hard capsules, soft capsules, powders, granules, orally disintegrating dosage forms effervescent tablets, chewable tablets, oral films or lyophilised dosage forms. The solid form can provide for immediate, sustained or controlled release of the active compound. In one of the embodiments the oral dosage form is an enteric-coated solid dosage form to provide protection of the compound from the acidic environment of the stomach. Solid dosage forms may be prepared following conventional manufacturing approaches such as wet granulation, direct compression or simple mixing of the active compound and the excipients. Additionally, liquid dosage forms such as syrups, drops and suspensions, wherein the active compound is dissolved or suspended respectively, are considered as suitable for this purpose. They may further contain drug targeting agents, bioavailability enhancement agents or active ingredients other than compounds of the invention.

Excipients that are commonly used for the preparation of solid dosage forms for oral administration are binding agents such as gelatin, natural gums, such as acacia, tragacanth; starches, sodium alginate, sugars, polyvinylpyrrolidone; cellulose derivatives such as hydroxypropylmethyl cellulose, polyvinyloxoazolidones; (pharmaceutical) fillers such as lactose, microcrystalline cellulose, dicalcium phosphate, tricalcium phosphate, calcium sulfate, dextrose, mannitol, sucrose; tableting lubricants if needed, such as calcium and magnesium stearate, stearic acid, talc, sterotex (alkaline stearate); disintegrants such as starch, starch derivatives and crosslinked polymers.

Essential excipients for the preparation of liquid dosage forms are solvents, co-solvents and other liquid carriers, such as water, ethanol, propylene glycol, polyethylene glycol; substances to increase the viscosity of the vehicle such as sugars, especially glucose, water swellable polymers such as cellulose derivatives (e.g. carboxymethylcellulose sodium) or polyvinylpyrrolidone; stabilizers preventing coagulation and caking of the suspension; preservatives such as parabens; other excipients for taste masking and taste improvement like sweeteners and flavours.

Surfactants may be used to enhance wetting and dissolution of the active compounds. Exemplary of useful surfactants are sodium lauryl sulfate, sorbitan monolaurate, sorbitan monostearate, polyoxyethylene (20) sorbitanmonooleate, polyoxyethylene (20) sorbitanmonooleate, poloxamer 407, poloxamer 188 (polyoxethylene, polyoxypropylene block polymers), polyoxyl 20 cetostearyl ether, dioctyl sodium sulfosuccinate, dioctyl calcium sulfosuccinate, nonoxynol, benzalkonium chloride, sorbitan monooleate.

Stabilizers may be incorporated to prevent the oxidation of gallic acid or gallic acid derivatives during storage, thus extending the shelf life of the composition.

In one embodiment, the compositions are formulated and processed for parenteral administration, preferably for intravascular injection, such as intravenous or intra-arterial, but also for intramuscular, subcutaneous, intralesional, intraperitoneal or other routes of parenteral administration. The formulation and manufacture of such compositions follow the same principles as applied to the formulation of other drug substances for these particular administration routes. As an example, sterility is one of the essential requirements for the preparation of parenteral dosage forms. Other requirements, such as pH value and osmolarity, are described in all major pharmacopoeias, such as in USP 24, in the monograph "General Requirements for Tests and Assays. 1. Injections". In order to improve the stability of a parenteral formulation it may be necessary to provide a dried dosage form which must be reconstituted before it can be administered. An example of such a dosage form is a freeze-dried or lyophilised formulation.

In an attempt to avoid frequent injections and to improve patient's compliance and the convenience of the therapy, it may be desirable to administer the compound of the invention as a parenteral controlled release dosage form. A variety of methods for preparing such depot formulations are extensively described in the literature. Prolonged release may be provided by solid implants, nanoparticles, nanocapsules, microparticles, microcapsules, emulsions, suspensions, oily solutions, liposomes or similar structures.

Due to tolerability issues, the use of excipients in parenteral formulations is somewhat limited. Nevertheless, excipients that are particularly useful for the preparation of parenteral formulations are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolarity and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilizers, antioxidants and preservatives, such as ascorbic acid, sodium sulfite or -hydrogen sulfite, EDTA, benzyl alcohol etc.; other excipients and lyophilization aids, such as albumin, dextran and the like.

If an active compound, such as a polyhydroxy phenol with affinity to P-selectin as disclosed above, shows chemical instability, e.g. in the fluids of the digestive system, or if its molecular weight is too high to be absorbed from the gut effectively, transmucosal administration may lead to an improved bioavailability of the compound compared to oral administration. This route of administration is at the same time non-invasive and patient-friendly. Transmucosal administration includes nasal, buccal, sublingual, gingival and vaginal dosage forms. These dosage forms can be prepared by established techniques; they can be formulated to represent nasal drops or sprays, inserts, films, patches, gels, ointments or tablets. Preferably the excipients used for a transmucosal dosage form include one or more substances providing for mucoadhesion, thus prolonging the contact time of the dosage form with the site of absorption and thereby potentially increasing the extent of absorption.

In a further embodiment the compounds are administered via the pulmonary route, using a metered dose inhaler, a nebuliser, an aerosol spray or a dry powder inhaler. Appropriate formulations can be prepared by known methods and techniques. Transdermal, rectal or ocular administration may also be feasible in some cases.

It can be advantageous to use advanced drug delivery or targeting methods in compositions according to the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances, such as cholic acid derivatives, phospholipids, ethanol, fatty acids, oleic acid, fatty acid derivatives, EDTA, carbomers, polycarbophil and chitosan.

As mentioned, the compositions comprising gallic acid or derivatives thereof may also be formulated as nutraceutical compositions, i.e. foods and beverages for the purpose of supporting the treatment or prevention of diseases and disorders linked to P-selectin activity according to the present invention. The beverages may include juices such as vegetable (e.g. carrot and tomato juice) and fruit juice (e.g. orange, apple, grape and pineapple juice); alcoholic beverages, such as beverages based on red, rose or white wine; teas (e.g. green tea); carbonated beverages; and beverages of supplementary nutrition (e.g. containing vitamins and vitamin complexes). Other nutraceutical compositions in the scope of the invention are sweets (e.g. chocolate and cookies); confectionary; olive oil; food products made from cereal flour like bread, crackers and noodles.

The amount of active ingredient to be incorporated into the compositions in accordance with the invention depends on several factors including the specifically intended use, the target users and the active compound, which is actually selected, i.e. whether it is a polyhydroxy phenol. In most cases the desired effects will be achievable with compositions containing 1 microgram of gallic acid or more. In another embodiment the composition comprises at least 10 mg and in another embodiment at least 100 or 500 mg. Of course, when derivatives with much higher anti P-selectin activity than gallic acid are used, the dose needs to be adjusted accordingly, such as to less than 100 mg, less than 10 mg or even less than 1 mg.

The active ingredient may be incorporated in pure form, as is typical for pharmaceutical products. Alternatively, if gallic acid or a natural derivative of gallic acid is used as active ingredient, the active compound may be incorporated in the form of a plant extract. The plant extract may be either liquid or solid-state, and numerous techniques are known and well-established to prepare such an extract. In one of the preferred embodiments a plant extract is used, which has been enriched in gallic acid or in at least one gallic acid derivative having affinity to P-selectin, which means that the process of preparing the extract has been designed, modified or optimised to have yield an especially large content of the compound(s) in question. The extract may, for instance, be prepared directly or indirectly from olives, red or white grapes or green tea. In a preferred embodiment it is prepared from red wine or red grapes.

In a further aspect, the invention relates to the use of a polyhydroxy phenol having the structural formula as shown above for the preparation of a medicament for inhibiting the activity of P-selectin in a subject which has developed a disease or condition in which P-selectin is involved or is at risk of developing such disease or condition.

As used herein, inhibition refers to any type of interaction which directly or indirectly leads to the modulation of the biological activity of P-selectin. Common types of inhibition include competitive, uncompetitive and non-competitive inhibition. Furthermore, inhibition may be described as reversible or irreversible. In practice, many inhibitory processes are of a competitive and reversible nature. Inhibition, in the broad definition used herein, also includes a type of interaction in which an initial phase of activation is observed, followed by a depression of bioactivity. Typically, an inhibitory effect can be found when an inhibitor binds with high affinity to the target molecule, whether the binding takes place in the same molecular region as the natural substrate (i.e. as a mimic) or not. In the case of P-selectin, different binding sites exist for various substrates. For instance, P-selectin glycoprotein ligand-1 (PSGL-1) binding involves a different pocket or site than that of sialyl Lewis X (sLeX). Without wishing to exclude other interactions between polyhydroxy phenols within the scope of the invention, it has been found by the inventors that gallic acid blocks the dynamic interaction between P-selectin and PSGL-1.

The subject to whom the polyhydroxy phenols are to be administered preferably is a human individual. However the compounds in accordance with the invention may, in principle, be applied to other subjects, such as mammals. The effectiveness thereof will depend on the affinity of the polyhydroxy phenols to the P-selectin molecule found in the specific species, as the sequence of this protein differs between species. It has been shown by the inventors, however, that e.g. gallic acid and other polyhydroxy phenols have a high affinity to human P-selectin, and they can be used to effectively modulate its activity, particularly as antagonists or partial antagonists.

The use of the polyhydroxy phenols in accordance with the invention requires that such compounds, having affinity to P-selectin, are administered in an effective amount. With regard to methods of identifying such polyhydroxy phenols which have affinity to P-selectin, useful examples are given in WO 03/020753, the disclosure of which is incorporated herein by reference. The exact amount or dose which needs to be administered in order to reduce the activity of P-selectin depends on various parameters, but can be determined by methods which are known to professionals skilled in this field. Reference is also made to WO 03/020753 and the literature quoted therein, which contains some information on methods of analysing the activity of P-selectin in an organism. Furthermore, the dose to be administered will, in any individual case, depend on factors such as the weight and age of the individual to whom the active material is to be administered, the severity of the conditions, symptoms, or risks which are to be reduced, the specific anti-P-selectin activity of the active compound or mixture of compounds which is used etc.

In the case of gallic acid itself for instance, it is desirable to achieve levels of the active compound at the site of action which are preferably at least in the micromolar range, i.e. at least 1 µM. Higher concentrations are preferred, such as at least 10 µM. From the evidence presently available it may be suggested that gallic acid levels of 10 µM at the site of action may be quite effective in blocking P-selectin substantially and doses which lead to such levels at the site of action are therefore preferred according to the invention. On the other hand, long-term studies may in the future also provide additional evidence that certain beneficial effects may be achieved with somewhat lower levels at the site of action, or that particularly beneficial effects may be achieved better with a higher degree of P-selectin achievable with levels of 10 µM or more at the site of action.

If other polyhydroxy phenols having affinity to P-selectin are used instead of gallic acid, it will be easy to the skilled person to determine or calculate dose equivalents for these compounds having the same physiological effect as certain gallic acid concentrations.

In most cases, the desired concentration of the active compound(s) at the site of action, as well as the degree of P-selectin inhibition which is aimed at, will be achieved with doses of more than 1 µg per day. In the case of gallic acid, the preferred dose range is from 1 µg to 10 g per day. In another embodiment, the daily dose is at least 10 mg, and in another embodiment it is at least 100 to 500 mg. Of course, when derivatives with much higher anti P-selectin activity than gallic acid are used, the dose per day which needs to be administered to achieve beneficial effects may be considerably less, such as less than 100 mg, less than 10 mg, or even less than 1 mg.

An important factor associated with the desired degree of P-selectin inhibition is whether the aim of using the compounds in accordance with the invention is to prevent or to treat a condition, symptom or disease associated with P-selectin activity. Over the past few years an increasing body of evidence has been generated that P-selectin is indeed associated with a number of pathological processes related to inflammation and cancer, and in particular to inflammatory processes leading to major diseases of the cardiovascular system. Among the conditions which are presently associated with P-selectin are coronary artery disease, thrombosis, cancer, chronic inflammatory disorders, rheumatoid arthritis, inflammatory bowel disease, multiple sclerosis, atherosclerosis, restenosis, ischemia, reperfusion injury including renal failure, tumor metastasis, bacterial sepsis, disseminated intravascular coagulation, adult respiratory stress syndrome, stroke, angiogenesis, transplant rejection, deep vein thrombosis, myocardial infarction and circulatory shock. Some of the mechanisms by which P-selectin may influence these conditions are described in more detail in: D. J. Lefer (Annu. Rev. Pharmacol. Toxicol. 40: 283-294 (2000)); R. W. McMurray (Semin. Arthritis Rheum. 25(4): 215-233 (1996))

In a preferred embodiment the use involves the administration of a polyhydroxy phenol to an individual which has already developed such a P-selectin associated disease, condition or symptom.

In another preferred embodiment the use in accordance with the invention involves the administration of a polyhydroxy phenol to an individual which may or may not already have developed a disease, condition or symptom associated with P-selectin activity, but which is at risk of developing such. In the broadest sense, any subject, which is not excluded from the risk categories and factors commonly associated with cardiovascular diseases, inflammatory diseases or neoplastic diseases which together represent the most important causes of death in the western societies, may be at risk and therefore benefit from the use in accordance with the invention. In this sense, such a subject may be a human being, typically a member of one of the western societies and preferably one who does not already—such as by virtue of any dietary habits—consume significant amounts of natural P-selectin inhibitors.

In another preferred embodiment the individual is at an increased risk of developing a disease, condition or symptom associated with P-selectin activity. An increased risk is typically defined as a risk substantially above the average risk of a reference group. Increased risks may be characteristics of individuals or of groups. For instance, individuals with certain personal dietary habits, such as high animal fat consumption, or heavy smokers may have a substantially increased risk of developing a cardiovascular disease such as coronary artery disease than the average peers. On the other hand, dietary factors influencing the cardiovascular risks may often also by characterised as national traits, such as the consumption of saturated fats and oils in some countries in which unsaturated vegetable oils are traditionally rather uncommon.

At a particularly high risk in the context of the present invention are those individuals who have already developed some symptoms—such as high blood pressure, hyperlipidemia or diabetes—which are frequently considered prodromal for the P-selectin associated diseases listed above. It is preferred that P-selectin inhibition by administering polyhydroxy phenols is performed on such individuals.

The administration of polyhydroxy phenols refers to any way of providing an individual with such compounds, whether by ingestion, also referred to as the (per)oral route of administration, or by any other route, such as mucosal, buccal, sublingual, lingual, nasal, rectal, vaginal, pulmonary, subcutaneous, dermal, transdermal, intramuscular, intraperitoneal, intravenous or intraarterial administration. The most common ways of administration are typically those which are associated with a high degree of consumer or patient preference and compliance. Hence, the most preferred way of administration according to the invention is by ingestion. A large number of product types, formulation techniques and dosage forms are available to suit almost any purpose and active ingredient which can be made bioavailable via the oral route. In another preferred embodiment, the polyhydroxy phenols are administered parenterally, preferably by injection, in particular by intravenous injection.

The present invention also relates to the use of polyhydroxy phenols having the structural formula as shown above as a medicament. More particularly it provides uses for pharmaceutical and nutraceutical compositions containing a polyhydroxy phenol with affinity to P-selectin. The uses are consistent with the methods of binding or inhibiting the activity of P-selectin, as described above, and include the diagnosis, prevention or treatment of a disease or condition selected from coronary artery disease, thrombosis, cancer, chronic inflammatory disorders, rheumatoid arthritis, inflammatory bowel disease, multiple sclerosis, atherosclerosis, restenosis, ischemia, reperfusion injury including renal failure, tumour metastasis, bacterial sepsis, disseminated intravascular coagulation, adult respiratory stress syndrome, stroke, angiogenesis, transplant rejection, deep vein thrombosis, myocardial infarction or circulatory shock.

According to the diagnostic use the compositions may be employed for in vitro tests to quantify P-selectin concentrations in body fluids and tissues (arterial lesions) as markers for the diseases and conditions associated with P-selectin. They may be also used for in vivo diagnostic imaging procedures to monitor P-selectin mediated atherosclerosis, restenosis, and other conditions selected from those in which P-selectin is mobilized. As an option for this use, a gallic acid molecule or derivative according to the invention may be conjugated with a chelator, which is subsequently complexed with an isotropic label that is detectable by the chosen monitoring system or associated with a contrast agent (DTPA chelated gadolinium or USPIO).

In terms of drug delivery, preferable embodiment is a targeting composition. The targeting composition of the present invention can be prepared into a variety of pharmaceutical preparations in the form of, e.g., a fatty emulsion, an emulsion, a liposome a micelle etc., and these preparations can be administered as intravascular, intramuscular or subcutaneous injection or as injection to the organ, or as an implant or as a transmucosal preparation through oral cavity, nasal cavity, rectum, uterus, vagina, lung, etc. The composition of the present invention can also be administered in the form of oral preparations (e.g., solid preparations such as tablets, capsules, granules or powders; liquid preparations such as emulsions or suspensions).

Where the composition is prepared into an injection, the composition may contain, if necessary and desired, a known preservative, stabilizer, emulsifying agent, oil base, dispersing agent, pH adjusters or isotonic agent. Examples of the preservative are glycerin, propylene glycol, phenol, benzyl alcohol, etc. Examples of the stabilizer are dextran, gelatin, tocopherol acetate, alpha-thioglycerin, etc. Examples of the emulsifying agent are DPPC, HSPC, DMPC, DSPC, DPPG, DMPG, purified egg yolk lecithin, purified soybean lecithin, PEG-lipid (e.g. PEG-DSPE), etc. Example of the oil base are purified soybean oil, purified sesame oil, etc. Examples of the dispersing agent include polyoxyethylene (20) sorbitan monooleate (Tween® 80), sorbitan sesquioleate (Span® 30), polyoxyethylene (160) polyoxypropylene (30) glycol (Pluronic® F68), polyoxyethylene hydrogenated castor oil 60, etc. Examples of the pH controller include hydrochloric acid, sodium hydroxide, etc. Examples of the isotonic agent are glucose, D-sorbitol, D-mannitol, glycerin, etc.

In this embodiment, the active compound may or may not be a P-selectin inhibitor. More typically, it will be a compound acting on the targeted cells or tissue via a different mechanism and the method will typically be applied when P-selectin inhibition alone is not sufficient to produce the desired effect. Chemically, the active compound may represent any class of compounds, such as natural, semisynthetic or synthetic small organic molecules, an inorganic substance, a peptide, a protein, a polysaccharide, or a nucleic acid such as an oligonucleotide, a DNA or RNA. Preferably, the active compound is either a nucleic acid or it is a compound with any type of inhibitory action on the target cell or tissue.

Target cells expressing P-selectin are platelets and activated endothelial cells. The following examples are intended to illustrate certain aspects and embodiments of the invention; however, they are not to be understood as to limit the scope of the claims as set forth below.

BRIEF DESCRIPTION OF THE DRAWINGS

FIG. 2 is a graphical representation of the P-selectin binding as compared to control of the compounds of examples 4, 5, 6 and 7 at different concentrations.

FIG. 3 shows a table listing the $IC_{50}$ values for the isomers of several compounds of examples 4, 5 and 7 of which the structural formula is also shown.

FIG. 4. Gallic acid (GA) antagonizes P-and L-selectin but not E-selectin. A. Competitive binding of GA-EWVDV (▲), EWVDV (+) and gallic acid (■) during the binding of TM11-PO to human P-selectin; B. Competition by gallic acid of the biotin-PAA-Le$^a$-SO$_3$ binding to human P-selectin (■), mouse P-selectin (□), human L-selectin (▲) and human E-selectin (▼) by gallic acid. Wells were coated with the selectins (0.3 μg/ml) and incubated with 0.33 μg/ml biotin-PAA-Le$^a$-SO$_3$ in the absence of presence of gallic acid. Values represent means±SEM of triplicate experiments.

FIG. 5. HL60 cell rolling over CHO—P cells is reduced by gallic acid. A. The number of adhering calcein-AM labeled HL60 cells on CHO—P cell coated coverslips at wall shear rates of 300 s$^{-1}$ (white bars) and 600 s$^{-1}$ (black bars), in the absence (control) or presence of gallic acid at the indicated concentrations, was determined from pictures taken during the experiment. For each, 26-30 pictures were analyzed in 2 independent perfusion assays (** $p<0.001$). B. The velocity (μm/s) of calcein-AM labeled HL60 cells rolling over CHO—P cells coated coverslips at wall shear rates of 300 s$^{-1}$ (white bars) and 600 s$^{-1}$ (black bars), in the absence (control) or presence of gallic acid (50 and 250 μM) was determined from real time movies. For each condition the rolling velocity of at least 20 individual HL60 cells was measured in 5-9 independent perfusion assays. Values represent mean±SEM (* $p<0.05$).

FIG. 8. Gallic acid reduces leukocyte-platelet tumbling in vivo. Dose-dependent inhibition of conjugate rolling over the femoral vein endothelium by gallic acid in C57/B16 mice (WT) expressed as number of conjugates rolling per unit of surface (A); Inhibition by gallic acid of the rolling of preformed conjugates between leukocytes and platelets in aged atherosclerotic mice (ApoE$^{-/-}$), expressed as percentage rolling in the absence of gallic acid (B).

FIG. 10. Maximal platelet aggregation in the presence of different concentrations of gallic acid (A) and EGCG (B).

EXAMPLES

Example 1

3,4,5-tri-O-(tert-butoxycarbonyl)-gallic acid

Figure 1:
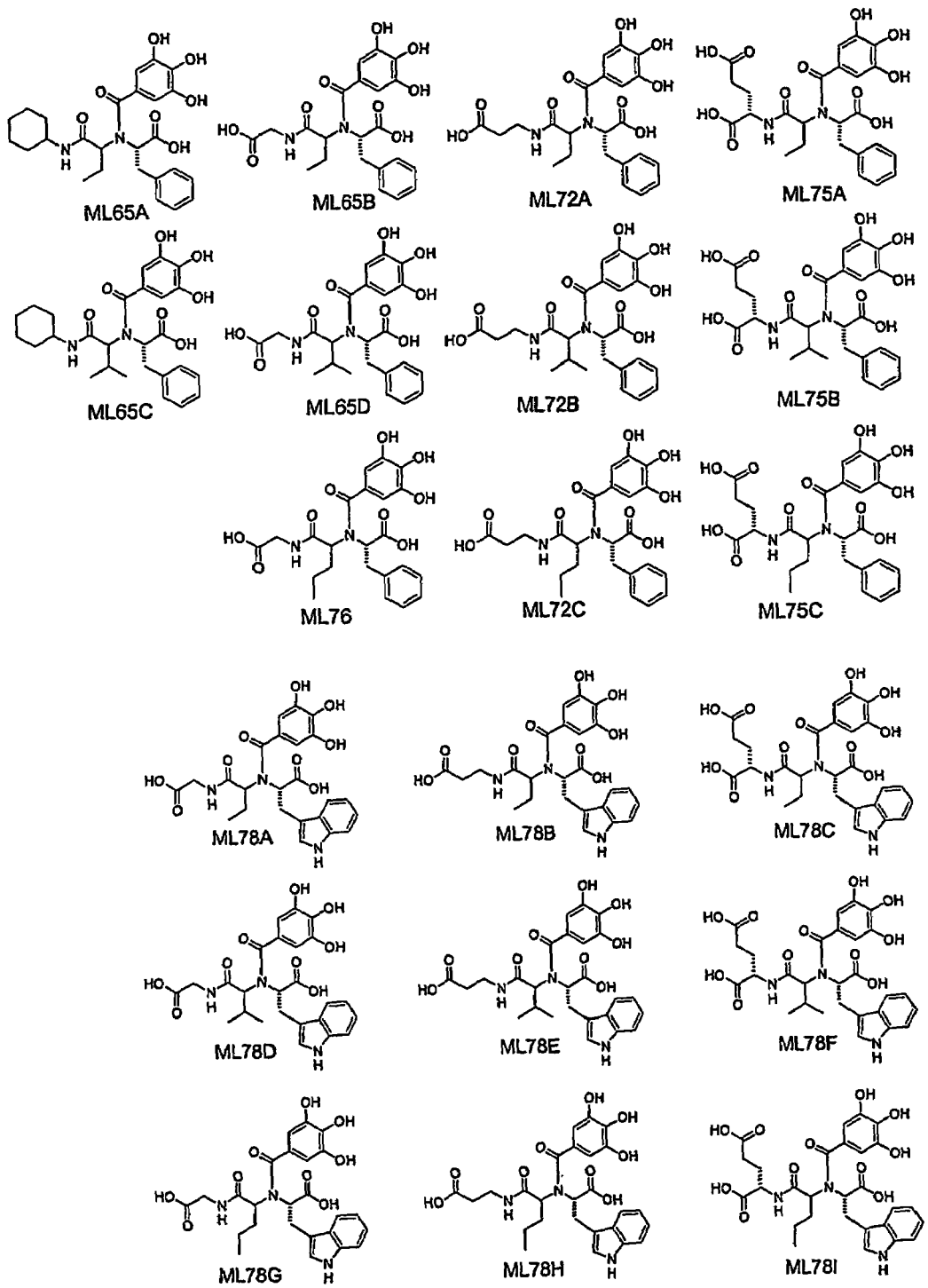
FIG. 1 provides the structural formula of the compounds of examples 4, 5, 6 and 7.
Figure 1:
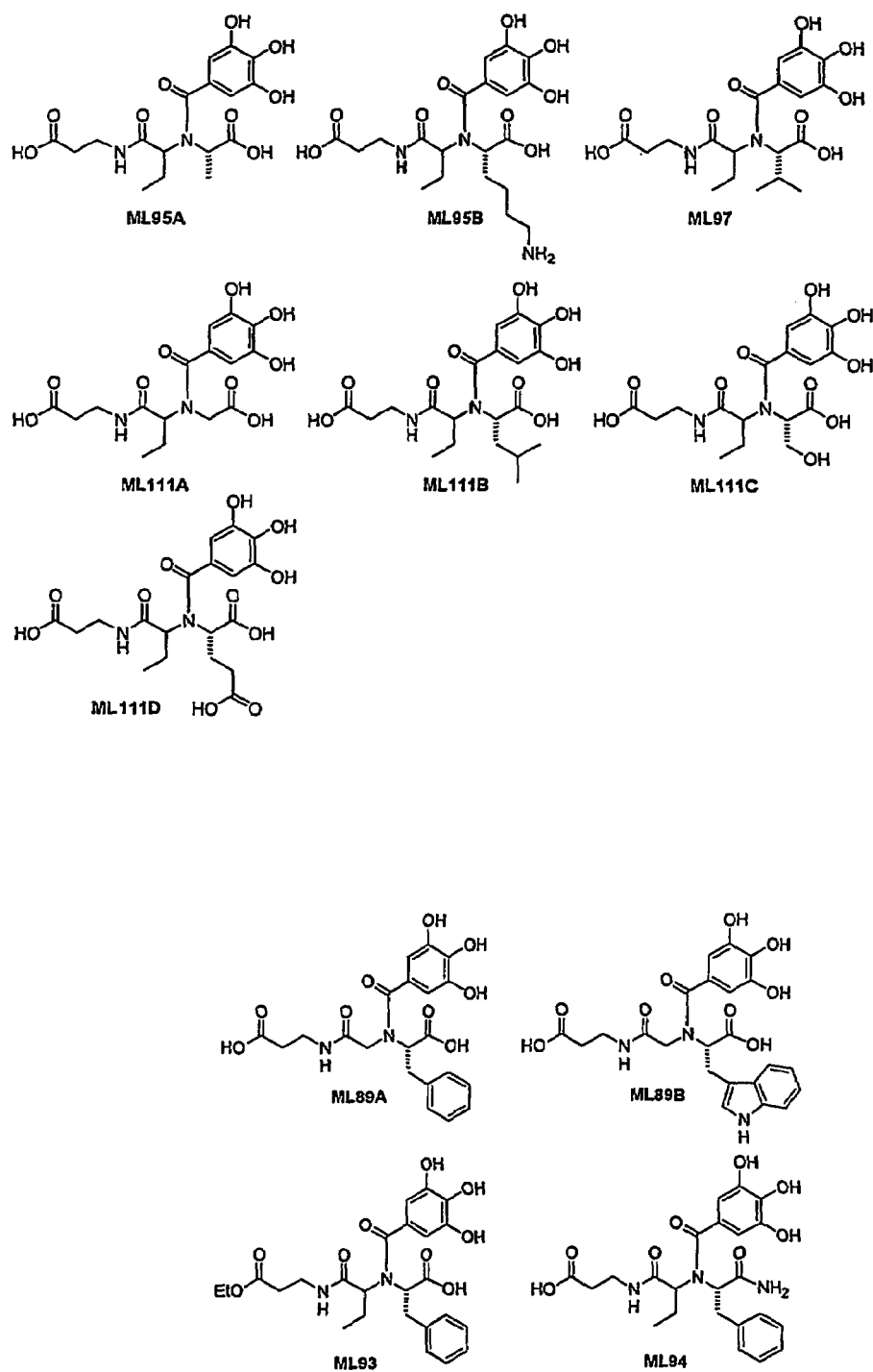
Figure 1:
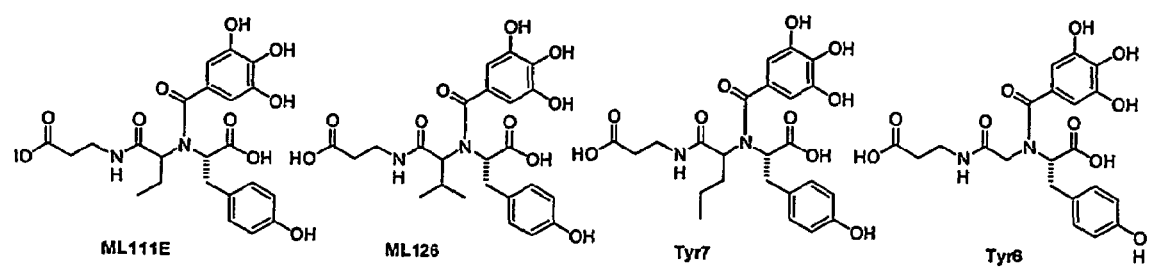

To gallic acid (5.0 g, 29.4 mmol) was added anhydrous DCM (60 mL). Nitrogen gas was bubbled through the inhomogeneous mixture for 5 minutes. Then, the mixture was treated subsequently with pyridine (88.2 mmol, 7.1 mL), di-tert-butyl dicarbonate (88.2 mmol, 19.2 g) and 4-dimethylaminopyridine (0.3 mmol, 37 mg). Gas evolution was observed and after 1 hour the mixture became homogeneous. After 2 hours, TLC analysis (eluent: ethyl acetate) revealed completion of the reaction. The reaction mixture was diluted with DCM (200 mL) and washed with 1 M HCl and water. The organic phase was dried on MgSO$_4$, then filtered and concentrated in vacuo. The residue was applied to a silica gel column and eluted with 10% ethyl acetate in toluene. Collection of the appropriate fractions afforded the title compound (9.26 g, 19.7 mmol, 67%) as a white solid.

$^{13}$C-NMR (50 MHz, CDCl$_3$) δ 169.9, 149.9, 148.6, 143.8, 139.7, 126.9, 122.2, 84.6, 84.5, 22.4; $^1$H-NMR (200 MHz, CDCl$_3$, TMS) δ 7.91 (s, 1H), 1.55 (s, 27H). MS (ESI) m/z 493.2 (M+Na), 963.4 (M+M+Na).

Reference Example 2

Synthesis of the Nitrites with Acid-Labile Protection

Tert-butyl isocyanoacetate was synthesised according to literature precedent: B. H. Novak and T. D. Lash, *J. Org. Chem.* 1998, 63, 3998-4010.

Tert-butyl isocyanopropionate was synthesised in two steps from commercially available β-alanine tert-butyl ester hydrochloride (NovaBiochem) as follows. To a solution of β-alanine tert-butyl ester hydrochloride (2 g, 11 mmol) in tetrahydrofuran (5 mL) and ethyl formate (5 mL) was added triethylamine (12 mmol, 1.7 mL). The flask was fitted with a reflux condenser and the mixture was heated for 4 hours, after which another quantity of ethyl formate was added (1 mL). An hour later, the mixture was filtered over silica gel. The silica gel was washed with ethyl acetate. The volatiles were removed from the filtrate, yielding N-formyl β-alanine tert-butyl ester (1.4 g, 11 mmol). $^{13}$C-NMR (50 MHz, CDCl$_3$) δ 171.2, 163.4, 80.8, 34.7, 33.4, 22.7; $^1$H-NMR (200 MHz, CDCl$_3$, TMS) δ 8.15 (s, 1H), 6.31 (broad s, 1H), 3.52 (q, 2H, J=6.1 Hz), 2.47 (t, 2H, J=6.2 Hz), 1.46 (s, 9H). This compound (0.65 g, 3.8 mmol) was subjected to the dehydration conditions described for the above nitrile to afford tert-butyl isocyanopropionate (0.50 g, 3.2 mmol, 85%) as a yellowish liquid. The colour darkened during storage at 4° C. (up to two months), but this did not greatly affect the quality of the product. $^1$H-NMR (200 MHz, CDCl$_3$, TMS) δ 3.64 (m, 2H), 1.48 (s, 9H).

Di-tert-butyl 2-S-isocyanopentanoate was synthesised in two steps from commercially available L-glutamic acid di-tert-butyl ester hydrochloride (NovaBiochem) in the same fashion as described for tert-butyl isocyanopropionate. Di-tert-butyl N-formyl-L-glutamate (white solid, 0.96 g, 3.33 mmol, 99% from L-glutamic acid di-tert-butyl ester hydrochloride): $^{13}$C-NMR (50 MHz, CDCl$_3$) δ 171.5, 170.3, 160.8, 81.7, 80.0, 50.3, 30.9, 27.5, 27.4, 27.1; $^1$H-NMR (200 MHz CDCl$_3$, TMS) δ 8.21 (s, 1H), 6.37 (broad d, 1 H), 4.64-4.54 (m, 1H), 2.41-1.76 (m, 4 H), 1.48 (s, 9H), 1.44 (s, 9H). Di-tert-butyl 2-S-isocyanopentanoate (0.41 g, 1.53 mmol, 90% from the formamide) was obtained as described above as a yellowish oil that solidifies upon storage. $^{13}$C-NMR (50 MHz, CDCl$_3$) δ 170.3, 164.7, 159.8, 83.1, 80.4, 55.8, 30.1, 27.5, 27.2; $^1$H-NMR (200 MHz, CDCl$_3$, TMS) δ 4.29 (dd, 1H, J$_1$=5.1 Hz, J$_2$=8.8 Hz), 2.50-2.42 (m, 2H), 2.32-2.02 (m, 2H), 1.50 (s, 9H), 1.46 (s, 9H).

Example 3

Experimental Procedure for Ugi Reaction

The Fmoc-protected amino acid was coupled to Tentagel resin equipped with the hydroxymethyl-phenoxyacetic acid (HMPA) linker via the standard procedure (DIC/DMAP in DCM/NMP). The loading of resin 1 was established via standard Fmoc-determination (typically 0.16 to 0.22 mmol/g).

All Ugi reactions were carried out on a 10 μmol scale. The Fmoc group on the amino group of 1 was removed by treatment with 20% piperidine in DMF for 15 minutes. After rinsing the resin with NMP (2×) and DCM (2×), aldehyde 2 (100 μmol) and anhydrous DCM (0.2 mL) were added. The resin was agitated for 1 hour. Then, a solution of tri-Boc-gallic acid (1, 100 μmol, 47 mg) in anhydrous MeOH (0.2 mL) and nitrile 4 (100 μmol) were added to the mixture. Shaking of the resin was continued for another 15 hours. The resin was then filtered, washed with NMP, MeOH and DCM (2× each). Cleavage from the solid support and deprotection of the product was attained by treatment of the resin with TFA/DCM (0.5/0.5 mL) containing triisopropylsilane (25 μL) for 2 hours. The resin was filtered off, rinsed with DCM, MeOH and DCM (2× each) and the filtrate evaporated at room temperature to obtain the crude Ugi product The identity and purity of the products were ascertained with LCMS (Alltima C18 column, using 10-90% acetonitrile in 0.05% TFA/H$_2$O, ESI-MS). Purification of active mixtures was done on an Alltima C-18 semi preparative column (250×10 mm), typically using a 30-50% gradient of acetonitrile in 0.1% TFA/H$_2$O, followed by lyophilization of the appropriate fractions.

DIC: diisopropylcarbodiimide
DMPA: 4-dimethylaminopyridine
DCM: dichloromethane
NMP: N-methylpyrrolidone
TFA: trifluoroacetic acid

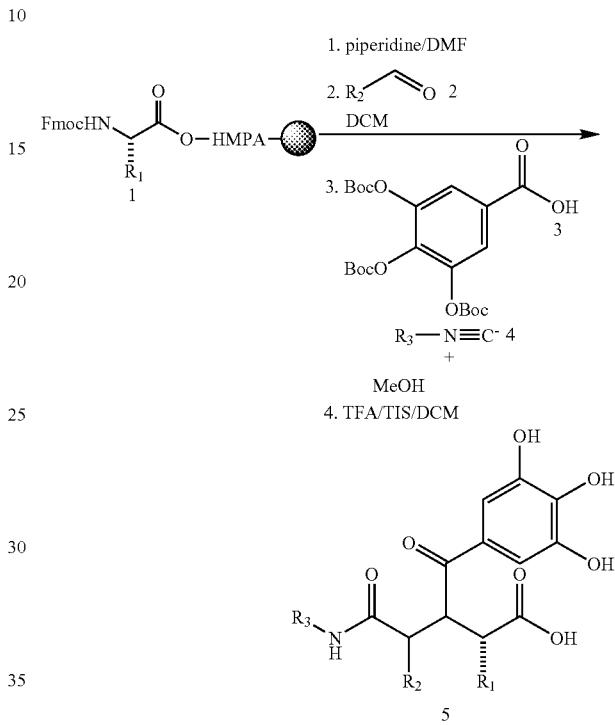

Example 4

Gallic Acid Derivatives Prepared from Phenylalanine

For the structural formulas the reader is referred to FIG. 1.

ML65A: (C$_{26}$H$_{33}$N$_2$O$_7$), MS(FT-ESI) m/z 485.22861 [M+H]$^+$
ML65B
ML65C
ML72A: (C$_{23}$H$_{27}$N$_2$O$_9$)
   diastereoisomer 1 MS(FT-ESI) m/z 475.17123 [M+H]$^+$
   diastereoisomer 2 MS(FT-ESI) m/z 475.17108 [M+H]$^+$
ML75A: (C$_{25}$H$_{29}$N$_2$O$_{11}$)
   diastereoisomer 1 MS(FT-ESI) m/z 533.17649 [M+H]$^+$
ML65D
ML72B
ML75B: (C$_{26}$H$_{31}$N$_2$O$_{11}$), MS(FT-ESI) m/z 547.19244 [M+H]$^+$
ML76
ML72C: (C$_{24}$H$_{29}$N$_2$O$_9$), MS(FT-ESI) m/z 489.18694 [M+H]$^+$
ML75C
ML89A
ML93
ML94

Example 5

Gallic Acid Derivatives Prepared from Tryptophane

For the structural formulas the reader is referred to FIG. 1.

ML78A
ML78B
ML78C: ($C_{27}H_{30}N_3O_{11}$)
   diastereoisomer 1 MS(FT-ESI) m/z 572.18754 $[M+H]^+$
   diastereoisomer 2 MS(FT-ESI) m/z 572.18759 $[M+H]^+$
ML78D
ML78E: ($C_{26}H_{30}N_3O_9$)
   diastereoisomer 1 MS(FT-ESI) m/z 528.19769 $[M+H]^+$
   diastereoisomer 2 MS(FT-ESI) m/z 528.19780 $[M+H]^+$
ML78F
ML78G: ($C_{25}H_{28}N_3O_9$), MS(FT-ESI) m/z 514.18246 $[M+H]^+$
ML78H:
   diastereoisomer 1 MS(FT-ESI) m/z 528.19773 $[M+H]^+$
   diastereoisomer 2 MS(FT-ESI) m/z 528.19752 $[M+H]^+$
ML78I: ($C_{28}H_{32}N_3O_{11}$), MS (FT-ESI) m/z 586.20339 $[M+H]^+$
ML89B

Example 6

Gallic Acid Derivatives Prepared from Tyrosine

For the structural formulas the reader is referred to FIG. 1.

ML111E: ($C_{23}H_{27}N_2O_{10}$), MS (FT-ESI) m/z 491.16629
ML126
Tyr7
Tyr6

Example 7

Other Gallic Acid Derivatives

For the structural formulas the reader is referred to FIG. 1.

ML95A
ML95B
ML97
ML111A
ML111B
ML111C
ML111D
ML89A
ML93
ML94

Example 8

Binding of SH31- to P-selectin in the Presence or Absence of an Inhibitory Polyhydroxy Phenol Crude mixtures of Ugi products were assayed for its ability to inhibit SH31-alkaline phosphatase (SH31-AP) binding to human P-selectin. SH31-AP, a tetrameric SH31/strepAP complex, which has previously been shown to bind with high affinity and specificity to human P-selectin (Molenaar, T. J. M. et al. Blood 2002; 100 (10):3570-3577), was freshly prepared by incubating streptavidin-AP (Amersham Life Science, Little Chalfont, UK; 5.0 µl 2.0 µM and SH31-biotin (biotin-VGLDPRDWVDVSDYA, 1.5 µl 190 µM) for 2 hours at room temperature in assay buffer (20 mM HEPES, 150 mM NaCl, 1 mM $CaCl_2$, pH 7.4). For competition studies, a 96 wells microtiter plate (high binding, flat bottom, Costar, Corning, U.S.A.) was coated overnight at 4° C. with 10 µg/ml goat anti-human IgG (Fc specific) (Sigma-Aldrich, Zwijndrecht, the Netherlands) in coating buffer (50 mM $NaHCO_3$, pH 9.6). Subsequently, wells were washed with assay buffer and incubated for 1 hour at 37° C. with blocking buffer (3% BSA in assay buffer). After washing with assay buffer, the wells were incubated for 2 hours at 37° C. with human P-selectin IgG-Fc chimera (R&D Systems Europe Ltd., Abingdon, United Kingdom; 0.3 µg/ml). Subsequently, wells were washed with assay buffer and incubated for 1 hour at 4° C. with the SH31-AP complex with or without Ugi products (10 or 100 µM). The wells were washed six times with assay buffer and substrate (0.6 mg p-nitrophenyl phosphate (PNP; Merck, Whitehouse Station, USA)/ml diethanolamine buffer (9.6% diethanolamine/ 0.35 mM $MgCl_2$ pH 9.8)) was added and wells were incubated at room temperature for 15 minutes. The reaction was halted by addition of 2.4 M NaOH and the absorbance was measured at 405 nm. The results are shown in FIG. 2. All the tested compounds dose-dependently inhibited the binding of SH31 to P-selectin.

Purified Ugi products were assayed for its ability to inhibit SH31-peroxidase (SH31-PO) binding to human P-selectin. SH31-PO, a tetrameric SH31/strepPO complex was freshly prepared by incubating streptavidin-PO (Amersham Life Science, Little Chalfont, UK; 5.0 µl 2.0 µM) and SH31-biotin (biotin-VGLDPRDWVDVSDYA, 1.5 µl 190 µM) for 2 hours at room temperature in assay buffer (20 mM HEPES, 150 mM NaCl, 1 mM $CaCl_2$, pH 7.4). For competition studies, a 96 wells microtiter plate (high binding, flat bottom, Costar, Corning, U.S.A.) was coated overnight at 4° C. with 10 µg/ml goat anti-human IgG (Fc specific; Sigma-Aldrich, Zwijndrecht, the Netherlands) in coating buffer (50 mM $NaHCO_3$, pH 9.6). Subsequently, wells were washed with assay buffer and incubated for 1 hour at 37° C. with blocking buffer (3% BSA in assay buffer). After washing with assay buffer, the wells were incubated for 2 hours at 37° C. with human P-selectin IgG-Fc chimera (R&D Systems Europe Ltd., Abingdon, United Kingdom; 0.3 µg/ml). Subsequently, wells were washed with assay buffer and incubated for 1 hour at 4° C. with the SH31-PO complex with or without Ugi products (range 0.4-100 µM). The wells were washed six times with easy buffer and substrate (3,3', 5,5'-tetramethylbenzine (TMB)/$H_2O_2$; Pierce, Rockford, USA) was added and wells were incubated at room temperature for 15 minutes. The reaction was halted by addition of 2 M of $H_2SO_4$ and the absorbance was measured at 450 nm. The results are shown in FIG. 3. IC50s for tested compounds are listed in FIG. 3 together with their chemical structure.

Example 9

Competition Assay of Gallic Acid with TM11-PO

Gallic acid (Acros, Geel, Belgium) was assayed for its ability to inhibit TM11-PO binding to human P-selectin. TM11-PO, a tetrameric TM11/strepPO complex, which has previously been shown to bind with high affinity and specificity to human P-selectin (Molenaar et al., Blood 2002, 100, 3570-3577), was freshly prepared by incubating streptavidin-peroxidase (strep-PO (Amersham Life Science, Little Chalfont, United Kingdom), 8.4 µl, 2.0 µM) and TM11-biotin (biotin-CDVEWVDVSSLEWDLPC (synthesised by Dr. Van der Zee, Department of Immunology, University of Utrecht, Utrecht, the Netherlands), 1.5 µl 190 mM) for 2 hours at room temperature in assay buffer (20 mM HEPES, 150 mM NaCl, 1 mM $CaCl_2$, pH 7.4). For competition studies, a 96 wells microtiter plate (high binding, flat bottom, Costar, Corning, U.S.A.) was coated overnight at 4° C. with 10 µg/ml goat anti-human IgG (Fc specific) (Sigma-Aldrich, Zwijndrecht, the Netherlands) in coating buffer (50 mM $NaHCO_3$, pH 9.6). Subsequently, wells were washed with assay buffer and incubated for 1 hour at 37° C. with blocking buffer (3% BSA in assay buffer). After washing with assay buffer, the wells were incubated for 2 hours at 37° C. with the human P-selectin IgG-Fc chimera (R&D Systems Europe Ltd., Abingdon, United Kingdom) (0.3 µg/ml). Subsequently, wells were washed with assay buffer and incubated for 1 hour at 4° C. with the TM11-PO complex. The wells were washed six times with washing buffer (0.1% Tween 20 in assay buffer). 3,3',5,5'-Tetramethylbenzamidine (TMB)/hydrogen peroxide ($H_2O_2$) (Pierce, Rochford, U.S.A.) was added and wells were incubated at room temperature for 15 minutes. The reaction was halted by addition of 2 M $H_2SO_4$ and the absorbance was measured at 450 nm.

The results are shown in FIG. 4A. In result, gallic acid was found to be a potent inhibitor of TM11-PO binding to human P-selectin with an $IC_{50}$ value of 7.2 µM.

Example 10

Competition Assay of Gallic Acid (Derivatives) with PAA-$Le^a$-$SO_3H$

To be able to test gallic acid binding also to other members of the selectin family (i.e. E- and L-selectin), biotin-PAA-$Le^a$-$SO_3H$ (Synthesone, Munich, Germany) instead of TM11-PO was used as ligand in the competition assay. This polyacrylamide (PAA) based polymer with attached sulfo-Lewis A groups, is an established selectin ligand.

Experimentally, the same procedure was used as in example 7 however with the following differences. After washing with assay buffer, the wells were incubated for 2 hours at 37° C. with the human P-selectin IgG-Fc chimera, mouse P-selectin IgG-Fc chimera, human L-selectin IgG-Fc chimera and human E-selectin IgG-Fc chimera respectively (all from R&D Systems Europe Ltd., Abingdon, United Kingdom) (0.3 µg/ml). Subsequently the wells of the microtiter plate were incubated with biotin-PAA-$Le^a$-$SO_3H$ (0.33 µg/ml) for 2 hours at 37° C., instead of with the TM11-PO-complex.

Gallic acid in this test was found to inhibit human P-selectin ($IC_{50}$ of approx. 85 µM). It was further found that gallic acid could not inhibit E-selectin binding, showing less than 20% inhibition at concentrations up to 1 mM, whereas it appeared to be a moderate inhibitor of L-selectin, with an $IC_{50}$ of 241 µM. Gallic acid binding to P-selectin appeared to be species-independent.

In addition to gallic acid itself, some derivatives of gallic acid (n-dodecyl gallate (Lancaster, Morecambe, United Kingdom) and (−)-epigallocatechin gallate (EGCG) (Sigma-Aldrich, Zwijndrecht, the Netherlands)), a polyphenol having anti-oxidant properties (caffeic acid) (Sigma-Aldrich, Zwijndrecht, the Netherlands) and 4-hydroxy benzoic acid (Acros, Geel, Belgium) were tested for their ability to inhibit human P-selectin. The results are shown in FIG. 4B. Of these compounds, EGCG was able to inhibit biotin-PAA-$Le^a$-$SO_3$ binding to human P-selectin having an $IC_{50}$ of 114 µM. All other compounds showed $IC_{50}$-values of >300 µM.

Example 11

Inhibition of Dynamic Interactions Between HL60 Cells and Human P-Selectin Expressing Chinese Hamster Ovary Cells Chinese hamster ovary (CHO) cells stably transfected with human P-selectin (CHO—P) were kindly donated by Dr. Modderman (University of Amsterdam, Amsterdam, the Netherlands). Cells were grown in DMEM (BioWhittaker Europe, Verviers, Belgium) containing 10% foetal calf serum (FCS) (BioWitthaker), 5 mM L-glutamine, 20,000 units penicillin/streptomycin (BioWhittaker) and 5 mM non-essential amino acids (Gibco, Paisley, United Kingdom). Flasks with cells were incubated at 37° C. in 5% $CO_2$ for 3 or 4 days until cells had grown nearly confluent.

HL60 cells were from ATCC and grown in RPMI 1640 medium (BioWhittaker) with 10% FCS, 5 mM L-glutamine and 20,000 units penicillin/streptomycin.

Dynamic interactions between macrophage-derived BL60 cells, displaying a high expression of PSGL-1, the natural P-selectin ligand, and human P-selectin expressing Chinese hamster ovary cell (CHO—P cells) monolayers grown onto glass coverslips coated with 30 µg/ml collagen S (type I) (Roche Diagnosis, Brussels, Belgium) were analysed in a parallel-plate perfusion chamber with a method adapted from G. Theilmeier (Blood 1999, 94: 2725-2734). The coverslip constituted the bottom of the chamber and the actual chamber was formed by a 254-µm height silicon rubber gasket designed with a conically shaped flow path, thus resulting in a 3-fold increase of wall shear rate from the inlet of the chamber to the outlet. Calcein-AM labeled HL60 cells, suspended in RPMI (0.5×106/ml) were perfused at 37° C. and at a flow rate of 1 ml/min with an inverted syringe pump (Harvard Instruments, South Natick, Mass., U.S.A.). The flow chamber was mounted on the table platform of an inverted epifluorescence microscope (Diaphot; Nikon, Melville, N.Y., U.S.A.) coupled to a Cohu CCD video camera (COHU Inc, San Diego, Calif., U.S.A.) and HL60 cell translocation over CHO—P monolayers were measured at wall shear rates of 300 and 600 s-1. Gallic acid was added to HL60 cell suspensions 2 minutes before the onset of perfusion. To prevent oxidation, the gallic acid solution was prepared freshly. Real time movies of 12 seconds (10 images per second), recorded at predefined positions in the flow path corresponding to chosen wall shear rates were stored and digitised with a Scion LG3 frame grabber (Scion Corp, Frederick, Mich., U.S.A.). The average velocity of HL60 cells rolling over the CHO—P cells was calculated from the rolling distance of the HL60 cells in a 1 second timeframe, using the NIH Image program version 6.1. The number of adhered HL60 cells was counted from pictures taken during the same experiment.

The results are shown in FIGS. 5A and 5B. As a result, gallic acid significantly decreased HL60 cell adhesion to the CHO—P monolayer already at 50 µM as compared to the untreated control, irrespective of the wall shear rates (300 $s^{-1}$ and at 600 $s^{-1}$, −34% and −43% respectively). At 250 µM, the effect of gallic acid was even more pronounced (−41% and −54% respectively).

The rolling velocity of the HL60 cells rolling across the CHO—P monolayer was measured in the same experimental set-up. The rolling velocity of HL60 cells was doubled in the presence of 50 and 250 µM of gallic acid.

Example 12

Platelet Isolation, Labelling and Preparation of Platelet Monolayer, Leukocyte Rolling Over Collagen Bound Platelet Monolayers Human blood was collected on 1:6 acid-citrate-dextrose (ACD: 93 mM trisodium citrate, 7 mM citric acid, 140 mM dextrose, pH 6.5) and 1 µM tirofiban. Human platelet rich plasma (PRP) was prepared via centrifugation at 150 g for 15 min. Murine blood was collected on 20 µg/ml hirudin and was centrifuged at 800 g for 30 sec, immediately followed by a second centrifugation at 150 g for 5 min to prepare PRP. The isolated PRP (human or murine) was then mixed with two volumes of ACD and recentrifuged at 800 g for 5 min. Subsequently, washed platelets were resuspended in HEPES-Tyrode's buffer (5 mM HEPES, 137 mM NaCl, 2.7 mM KCl, 12 mM NaHCO$_3$, 0.36 mM NaH$_2$PO$_4$, 1% (w/v) glucose, pH 7.3) containing 1% (v/v) human serum albumin (HAS) at $10^6$ platelets/µl. They were then incubated for 20 min at 37° C. with 5 µM calcein-AM, an acetoxymethyl ester, fluorescent once cleaved by non-specific esterases inside the cell, with no detectable effect on platelet function in our perfusion studies. The platelet suspension was then centrifuged at 700 g for 25 min and fluorescent platelets were resuspended in HEPES-Tyrode's buffer, and murine platelets were injected as such in mice.

A human platelet carpet for subsequent perfusion studies was made by overnight coating of glass coverslips with calf skin collagen, dissolved in 50 mM acetic acid at 1 mg/ml. Coverslips were then rinsed in complete Tyrode's buffer (Tyrode buffer containing 2 mM CaCl$_2$, 1 mM MgCl$_2$ and 1% human albumin). Whole human blood, anticoagulated with 20 µg/ml hirudin was then reperfused over the collagen coated surface in a parallel flow chamber at a shear rate of 300 s$^{-1}$, in the presence of 1 mM tirofiban (Merck). In these conditions, a homogeneous carpet of activated spread platelets forms on the coverslips, without formation of platelet aggregates.

Figure 6:
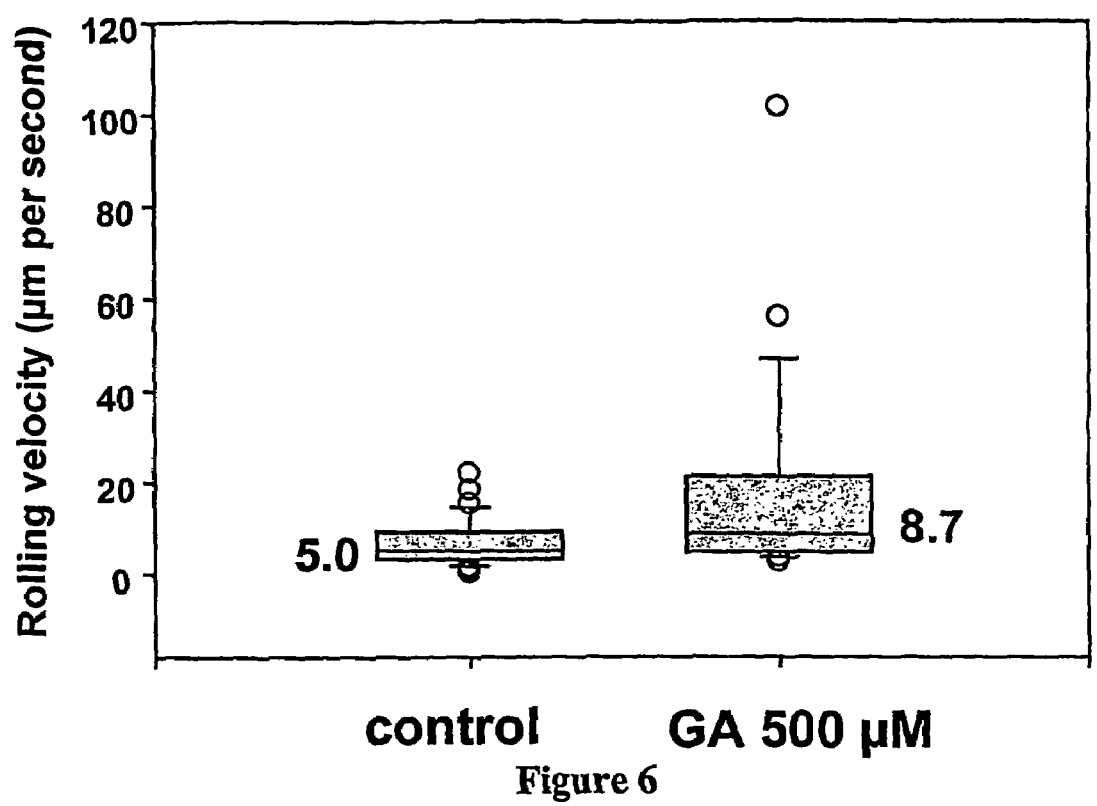
FIG. 6. Leukocyte rolling over monolayers of platelets in vitro. Box plot representation of the distribution of velocities during the rolling of resting blood leukocytes over a surface consisting of human platelets adhered to calf skin collagen at a shear rate of 150 s$^{-1}$, in the absence (control, number of cells analysed=35) or presence of 500 μM gallic acid (GA500, number of cells analysed=22). The mean rolling velocities for both groups are indicated (μm/sec, $p<0.05$).
Figure 7:
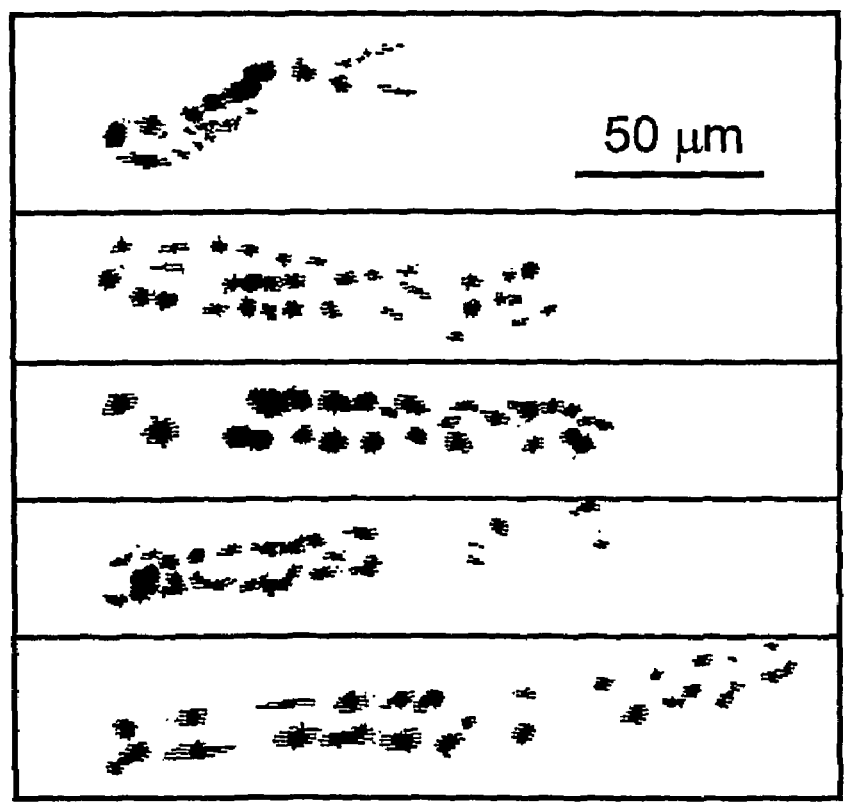
FIG. 7. Dynamic tumbling of leukocyte-platelet conjugates over femoral vein endothelium in vivo. Overlay plot of on-line registered images for 5 individual conjugates between mouse leukocytes and fluorescent-labeled collagen-activated mouse platelets, in the presence of the $α_{IIb}β_3$ antagonist G4120. Image interval represents 0.1 sec. The distance travelled is indicated via the scale bar. Leukocytes are non-labeled; leukocyte-bound platelets are labeled as black dots.

Following perfusion of whole blood anticoagulated with 20 µg/ml hirudin in a flow chamber, at a shear rate of 300 s$^{-1}$ during 5 min at 37° C. to produce carpets of collagen-bound platelet monolayers, the blood was progressively washed-out with complete tyrode buffer containing 1% human albumin. Perfusion was continued at a constant shear rate of 150 s$^{-1}$, in the presence or absence of either 500 µM gallic acid or 25 µg/ml of the anti-P-selectin antibody WAPS12.2. After 3 min of washing, remaining leukocytes translocating over the platelet carpet were visualized with an inverted microscope, movies were captured in the memory of an attached computer and the translocation velocity was calculated, as mentioned above. Results are shown in FIGS. 6 and 7.

Example 13

In Vivo Inhibition of Endothelial Cell Inflammation

Figure 9:
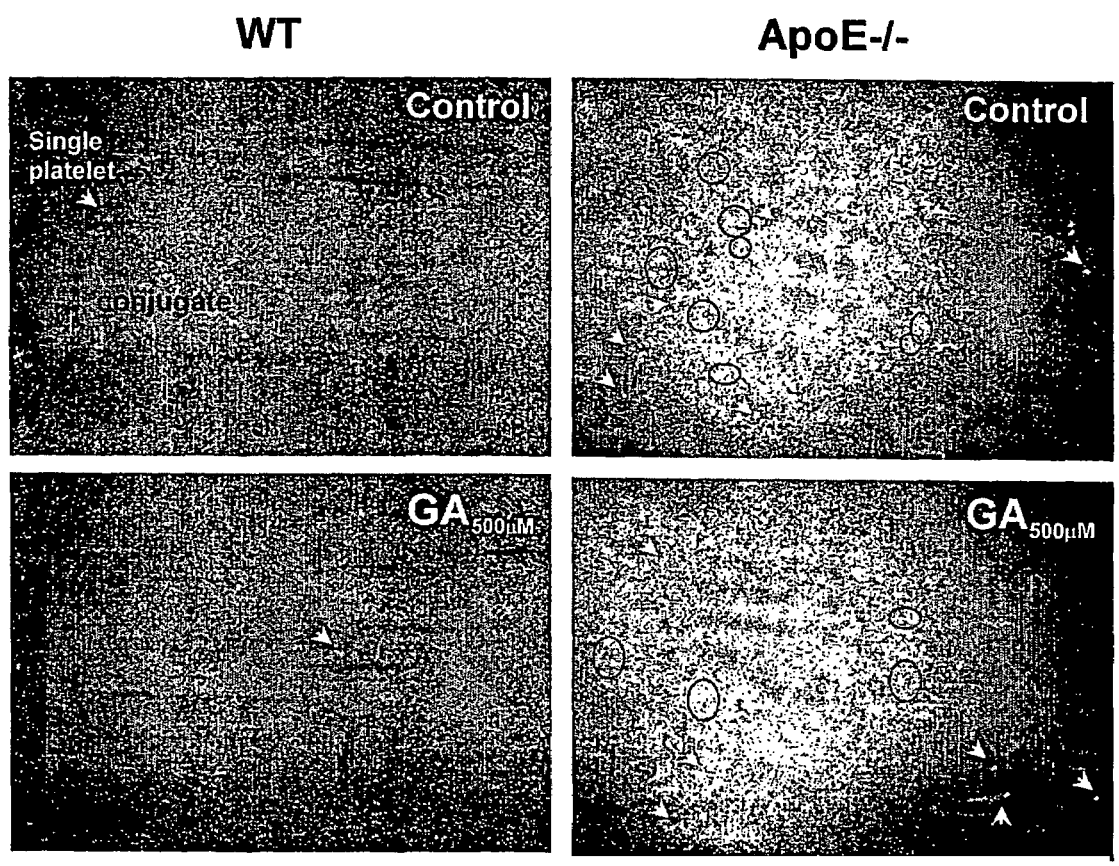
FIG. 9. Conjugate rolling and platelet adhesion in control and atherosclerotic mice. Adhesion of single platelets (identified by arrows) and rolling of conjugates (identified by leukocyte-bound platelets encircled in red) in nontreated mice (WT) and atherosclerotic mice (ApoE$^{-/-}$), in the absence (control) or presence of 500 μM gallic acid (GA).

All animal experiments were reviewed and approved by the Institutional Review Board of the University of Leuven and were performed in compliance with the guidelines of the International Society on Thrombosis and Haemostasis (Giles AR). For the study of platelet-assisted leukocyte rolling over the endothelial surface of blood vessels in vivo, on-line video microscopy was performed in mice. C57AB16 mice (6-12 weeks old) were anesthetized with Nembutal (70 mg/kg) via i.p. injection, and the jugular vein was catheterized. The femoral vein was exposed and mice were positioned on the table of an inverted epifluorescent microscope, such that the blood circulation in the femoral vein could be visualized through a Cohu CCD video camera. Fluorescent-labeled murine platelets were then injected in the catheterized jugular vein (500×10$^6$ platelets in 200 µl) and baseline rolling was recorded for the labeled platelets. After 10 min, 50 µg/kg collagen was injected to activate circulating platelets, under protection of the anti-$\alpha_{IIb}/\beta_3$ antagonist G4120, which was injected together with collagen at 1 mg/kg to prevent activated platelets from aggregating. After 5 min, the collagen-induced rolling and tumbling of leukocyte-platelet conjugates was then recorded for 10 min. The number of rosettes rolling were counted and their average tumbling speed was calculated from the registered movies. To address the effect of gallic acid on rosette rolling, it was infused 5 min prior to collagen administration and the rosette rolling was analysed as in the controls. Rosette-vessel wall interactions were also studied in the femoral vein of aged atheroslerotic ApoE$^{-/-}$ mice (>1 yr). Tumbling rosettes were counted 10 min after the collagen injection, before and after gallic acid infusion of 0.75 to 7.5 mg/kg.h. The dose giving a half maximal inhibition of rosette tumbling (ED50) was calculated to be 1.5±0.4 mg/kg.h, which corresponds with an effective plasma concentration of 40 µM. Results are shown in FIGS. 8A, 8B and 9.

Example 14

Effect of a Polyhydroxy Phenol on Platelet Aggregation

GA and EGCG (as a reference) were tested for their effects on platelet aggregation. Due to its tendency to form micelles DG could not be used in these experiments as it causes platelet lysis.

Freshly drawn venous blood from healthy volunteers was collected with an informed consent into 1/10 volume of 3.2% tri-sodium citrate (w/v). These donors denied to have taken aspirin or other platelet function inhibitors during the previous ten days. Platelet-rich plasma (PRP) was prepared by centrifugation (150 g, 15 min, 22° C.). PRP was adjusted to a final concentration of 200,000 platelets/µl with platelet-poor plasma (PPP), which was obtained after an additional centrifugation step of the remaining blood (1100 g, 15 min, 22° C.). PRP was left for 30 min at 37° C. to ensure a resting state of the platelets. Afterwards, PRP was incubated for 5 min with different concentrations of gallic acid, EGCG or solvent at 37° C. Samples were transferred to an aggregometer (Kordia BV, Leiden, The Netherlands) to determine platelet aggregation at a stirring speed of 900 r.p.m. Platelet aggregation was initiated after preincubation with different concentrations of GA or EGCG (0, 50, 250 and 500 µM) by the addition of thrombin receptor activating peptide (TRAP, 6.5 µM, 37° C.).

Maximal aggregation is depicted in FIGS. 10(A) for GA and in 10(B) for EGCG. It was found that both GA and EGCG inhibit platelet aggregation significantly at a concentration of 500 µM. At a concentration of 250 µM no significant inhibition was measured, resulting from a large interindividual variability in the response to gallic acid between the donors.

Example 15

Emulsion Preparation

After 0.5 part of ML72A (a polyhydroxy phenol derivative) and 0.4 part of dexamethasone palmitate and 1.2 part of Purified egg yolk lecithin and 10 parts of purified soybean oil were added in 2.21 part of concentrated glycerin and 85.69 parts of water, an emulsion preparation was prepared using a microfluidizer (12,000 psi, 10 minutes at room temperature).

The invention claimed is:

1. A polyhydroxy phenol of structural formula:

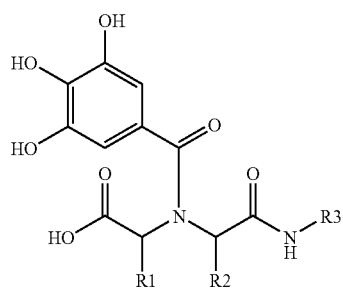

wherein:
$R^1$=a hydrogen; a straight or branched ($C_1$-$C_4$) aliphatic alkyl group or an aromatic group, optionally respectively substituted by a hydroxyl group, a carboxylic acid group, an amino group or a straight or branched ($C_1$-$C_4$) aliphatic alkyl group;
$R^2$=a hydrogen; a straight or branched ($C_1$-$C_4$) aliphatic alkyl group; and
$R^3$=a straight or branched ($C_1$-$C_4$) aliphatic alkyl group, optionally substituted by one or more carboxylic acid group, or a straight or branched ($C_1$-$C_4$) aliphatic alkyl amide group; or a ($C_3$-$C_8$) cycloalkyl group, optionally substituted by a straight or branched ($C_1$-$C_4$) aliphatic alkyl group or one or more carboxylic acid group.

2. The polyhydroxy phenol according to claim 1, wherein:
$R^1$=ethyl, phenylmethyl, indolylmethyl or 4-hydroxyphenylmethyl;
$R^2$=a R straight ($C_1$-$C_4$) aliphatic alkyl group; and
$R^3$=a straight ($C_1$-$C_4$) aliphatic alkyl group, substituted by one or two carboxylic acid groups, optionally substituted by a straight or branched ($C_1$-$C_4$) aliphatic alkyl group.

3. The compound according to claim 2, wherein:
$R^1$=ethyl, phenylmethyl, indolylmethyl or 4-hydroxyphenylmethyl;
$R^2$=hydrogen, ethyl, propyl or isopropyl; and
$R^3$=ethylcarboxylic acid or propyldicarboxylic acid.

4. 3,4,5-tri-O-(tert-butoxycarbonyl)-gallic acid.

5. A process for the preparation of the polyhydroxy phenols according to claim 1 comprising combining an amino acid, an aliphatic aldehyde, a nitrile and a gallic acid providing moiety, wherein 3,4,5-tri-O-(tert-butoxycarbonyl)-gallic acid is the gallic acid providing moiety.

6. A composition comprising (a) one or more polyhydroxy phenols according to claim 1 and (b) at least one pharmaceutically acceptable excipient.

7. A composition comprising (a) one or more of the polyhydroxy phenols according to claim 1, gallic acid or a derivative thereof or a polyphenol (b) an active ingredient, which is a drug, a contrast agent or a radionuclide, and (c) at least one pharmaceutically acceptable excipient.

8. The composition according to claim 7, wherein the component of part (a) is conjugated or coupled to the active ingredient, optionally through a linker.

9. The composition according to claim 7, wherein the component of part (a) has been incorporated into or anchored onto entities, which are lipid vesicles, emulsion droplets, polymers, proteins, nano-or microparticles, hydrogels, complexes, or virosomes.

* * * * *